(12) United States Patent
Chang et al.

(10) Patent No.: US 10,344,065 B2
(45) Date of Patent: Jul. 9, 2019

(54) METHOD FOR TREATING ALZHEIMER'S DISEASE AND METHOD FOR DOWNREGULATING PROTEIN AGGREGATION IN BRAIN

(71) Applicant: National Cheng Kung University, Tainan (TW)

(72) Inventors: Nan-Shan Chang, Tainan (TW); Yu-Min Kuo, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 15/912,634

(22) Filed: Mar. 6, 2018

(65) Prior Publication Data
US 2019/0161525 A1 May 30, 2019

Related U.S. Application Data

(60) Provisional application No. 62/590,430, filed on Nov. 24, 2017.

(51) Int. Cl.
| | |
|---|---|
| *C07K 7/06* | (2006.01) |
| *A61K 38/08* | (2019.01) |
| *A61K 38/17* | (2006.01) |
| *A61P 25/28* | (2006.01) |
| *C07K 14/47* | (2006.01) |

(52) U.S. Cl.
CPC .......... *C07K 14/4747* (2013.01); *A61K 38/08* (2013.01); *A61K 38/1761* (2013.01); *A61P 25/28* (2018.01); *A61K 38/1709* (2013.01); *C07K 7/06* (2013.01)

(58) Field of Classification Search
CPC ...... C07K 7/06; C07K 14/47; C07K 14/4747; C07K 14/4703; A61K 38/08; A61K 38/1709; A61K 38/1761; A61P 25/28
See application file for complete search history.

(56) References Cited

U.S. PATENT DOCUMENTS

| | | | |
|---|---|---|---|
| 9,546,354 B2 * | 1/2017 | Chang | C12N 5/0648 |
| 2014/0135272 A1 * | 5/2014 | Chang | C07K 7/08 |
| | | | 514/19.3 |

OTHER PUBLICATIONS

Xu J et al. Gain of function of mutant p53 by coaggregation with multiple tumor suppressors. Nature Chem Biol. 7, 285-295. (Year: 2011).*

Lee MH, Shin YH, Lin SR, Chang JY, Lin YH, Sze CI, Kuo YM, Chang NS, Zfra restores memory deficits in Alzheimer's disease tripletransgenic mice by blocking aggregation of TRAPPC6AΔ,SH3GLB2, tau, and amyloid β, and inflammatory NF-κB activation, Alzheimers Dement (N Y). Mar. 6, 2017;3(2):189-204.

* cited by examiner

*Primary Examiner* — Kimberly Ballard
(74) *Attorney, Agent, or Firm* — Bacon & Thomas, PLLC

(57) ABSTRACT

A method for treating Alzheimer's disease and a method for downregulating protein aggregation in brain are disclosed, which respectively comprises: administering a zinc finger-like peptide to a subject in need thereof, wherein the zinc finger-like peptide comprises an amino acid sequence of RRSSSCK (SEQ ID NO: 1).

3 Claims, 25 Drawing Sheets

Specification includes a Sequence Listing.

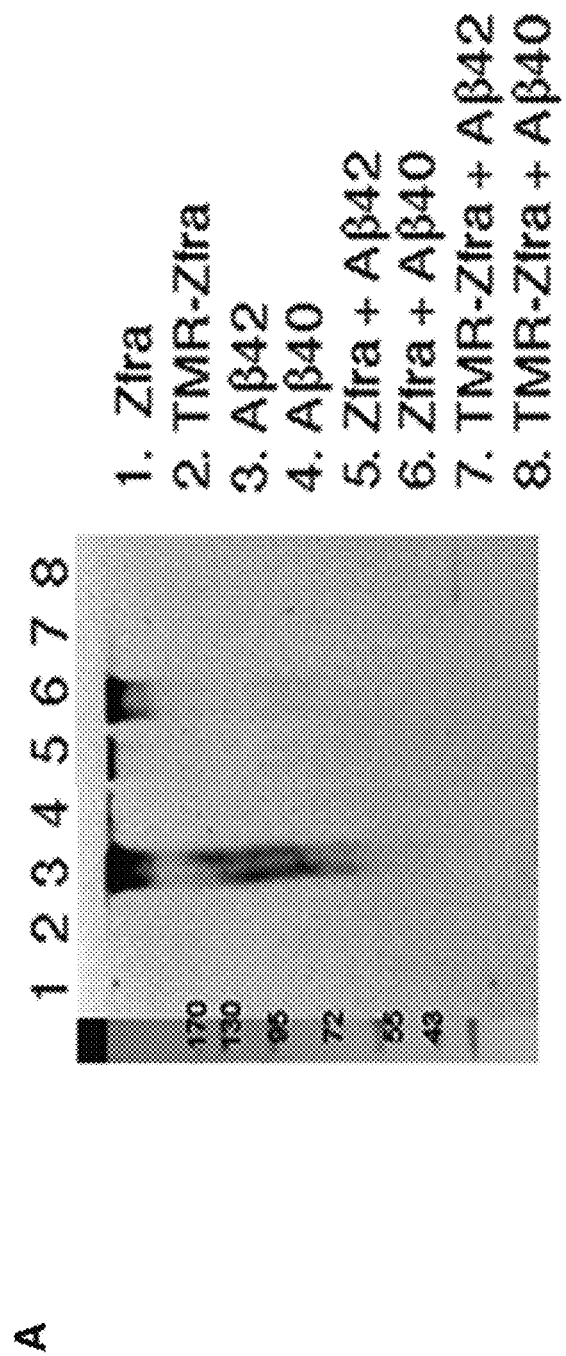

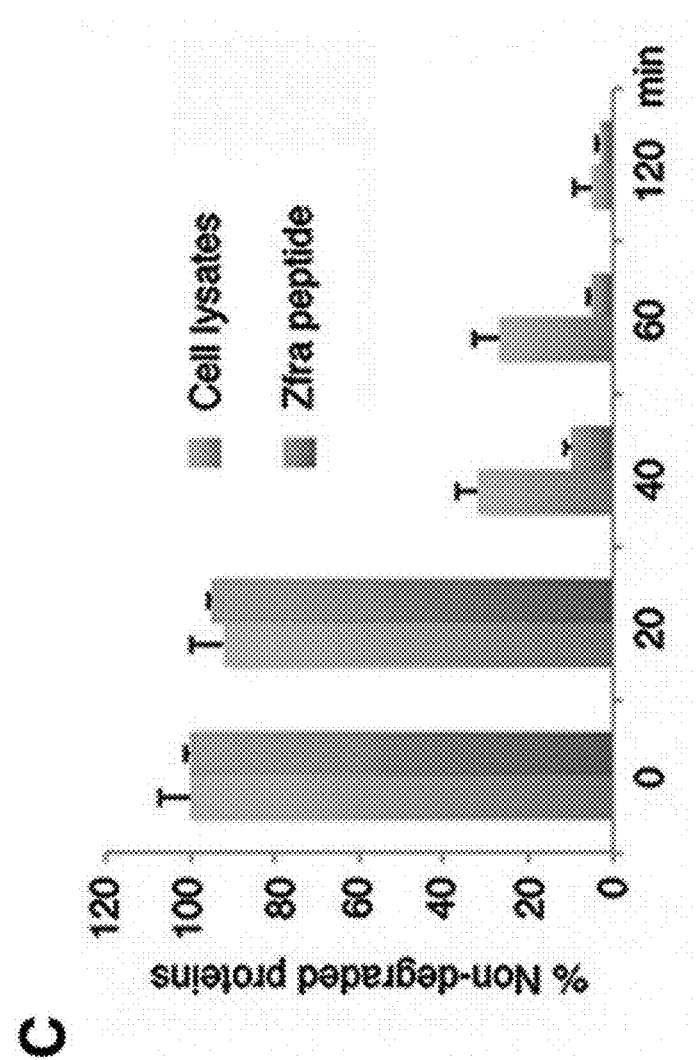
Fig. 6 (Cont' d)

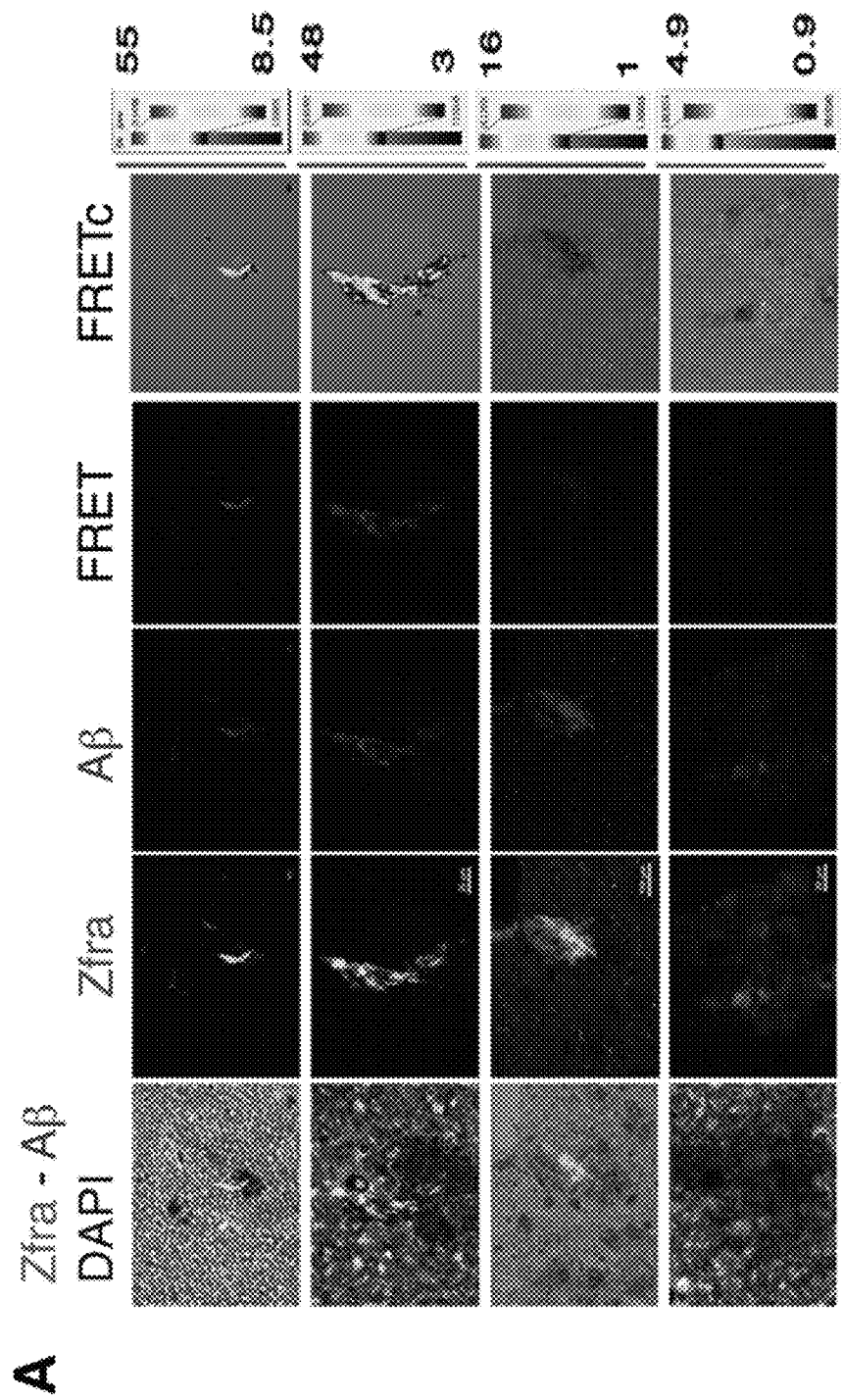

METHOD FOR TREATING ALZHEIMER'S DISEASE AND METHOD FOR DOWNREGULATING PROTEIN AGGREGATION IN BRAIN

CROSS REFERENCE TO RELATED APPLICATION

This application claims the benefit of filing date of U. S. Provisional. Application Ser. No. 62/590,430, filed Nov. 24, 2017 under 35 USC § 119(e)(1).

BACKGROUND

1. Field

The present disclosure relates to a method for treating Alzheimer's disease and a method for downregulating protein aggregation in brain.

2. Description of Related Art

Abnormal protein aggregation or inclusion is present in most age-related neurodegenerative diseases, wherein abnormal β-amyloid (Aβ) aggregation is the most common abnormal protein aggregation. Furthermore, abnormal β-amyloid aggregation causes Alzheimer's disease (AD). Alzheimer's disease is the most well-known form of dementia and it causes memory loss and progressive cognitive decline. However, there is no drug for curing Alzheimer's disease at the moment, and the existing treatments for AD can merely preserve or improve cognitive function and reduce behavioral disorders to delay disease progression. As a result, there is an urgent need to find methods for treating or delaying Alzheimer's disease.

Pathological features of Alzheimer's disease include extracellular amyloid and intracellular neurofibrillary tangle, wherein the main component of extracellular amyloid is β-amyloid. Furthermore, β-amyloid deposition increases oxidative stress and thus leads to death of nerve cells. Hence, the level of deposition is strongly relevant to neurotoxicity. Therefore, it is desirable to provide a method for inhibiting abnormal β-amyloid aggregation, or a method for treating or effectively delaying neurodegenerative diseases related to abnormal β-amyloid aggregation such as Alzheimer's disease.

SUMMARY

The present disclosure is based on an unexpected discovery that a zinc finger-like protein can downregulate protein (such as TRAPPC6AΔ (trafficking protein particle complex 6A delta, TPC6AΔ), SH3GLB2, tau, or amyloid β) aggregation, especially abnormal protein aggregation which may result plaque formation in brain, in a subject. Therefore, the zinc finger-like protein can be used as a candidate for treating Alzheimer's disease.

Accordingly, the present disclosure provides a method for downregulating protein aggregation in brain, comprising: administering an effective amount of a zinc finger-like peptide to a subject in need thereof, wherein the zinc finger-like peptide comprises an amino acid sequence of RRSSSCK (SEQ ID NO: 1).

The present disclosure provides a method for treating Alzheimer's disease, comprising: administering an effective amount of a zinc finger-like peptide to a subject in need thereof, wherein the zinc finger-like peptide comprises an amino acid sequence of RRSSSCK (SEQ ID NO: 1).

The present disclosure provides a pharmaceutical composition for downregulating protein aggregation in brain, comprising: an effective amount of zinc finger-like peptide comprising an amino acid sequence of SEQ ID NO: 1.

The present disclosure provides a pharmaceutical composition for treating Alzheimer's disease, comprising: an effective amount of zinc finger-like peptide comprising an amino acid sequence of SEQ ID NO: 1.

In addition, the present disclosure provides a use of zinc finger-like peptide in manufacturing a medicament for downregulating protein aggregation in brain, wherein the zinc finger-like peptide comprises an amino acid sequence of SEQ ID NO: 1.

Furthermore, the present disclosure also provides a use of zinc finger-like peptide in manufacturing a medicament for treating Alzheimer's disease, wherein the zinc finger-like peptide comprises an amino acid sequence of SEQ ID NO: 1.

In the methods, the pharmaceutical compositions or the uses of the preset disclosure, the sequence of the zinc finger-like peptide is not particularly limited, as long as 7 continuous amino acids have the amino acid sequence of SEQ ID NO: 1.

For example, in one aspect of the present disclosure, the zinc finger-like peptide may only have 7 amino acids having the amino acid sequence of SEQ ID NO: 1. In another aspect of the disclosure, the zinc finger-like peptide may have the more than 7 amino acids, for example, the zinc finger-like peptide is a peptide having an amino acid sequence of SEQ ID NO: 2 (MSSRRSSSCKYCEQDFRAHTQKNAATPFLAN).

In the methods, the pharmaceutical compositions or the uses of the preset disclosure, the protein aggregation may be TRAPPC6AΔ, SH3GLB2, tau, or amyloid β aggregation, which may result in plaque formation in brain.

Other novel features of the disclosure will become more apparent from the following detailed description when taken in conjunction with the accompanying drawings.

Zfra versus respective PBS group, two-tailed unpaired t-test (PBS group, n=3; Zfra group, n=5).

Figure 3:
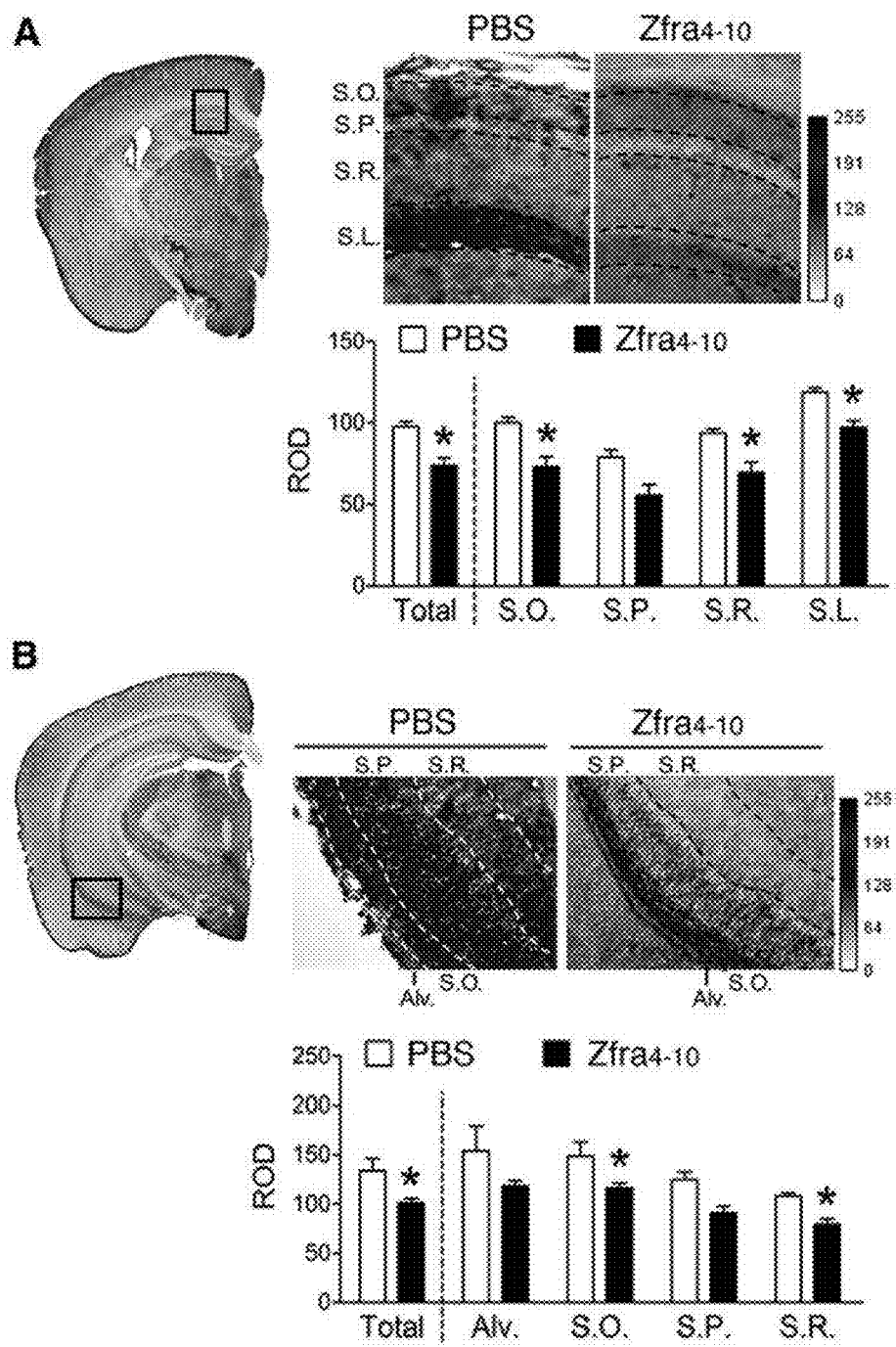
Figure 3:
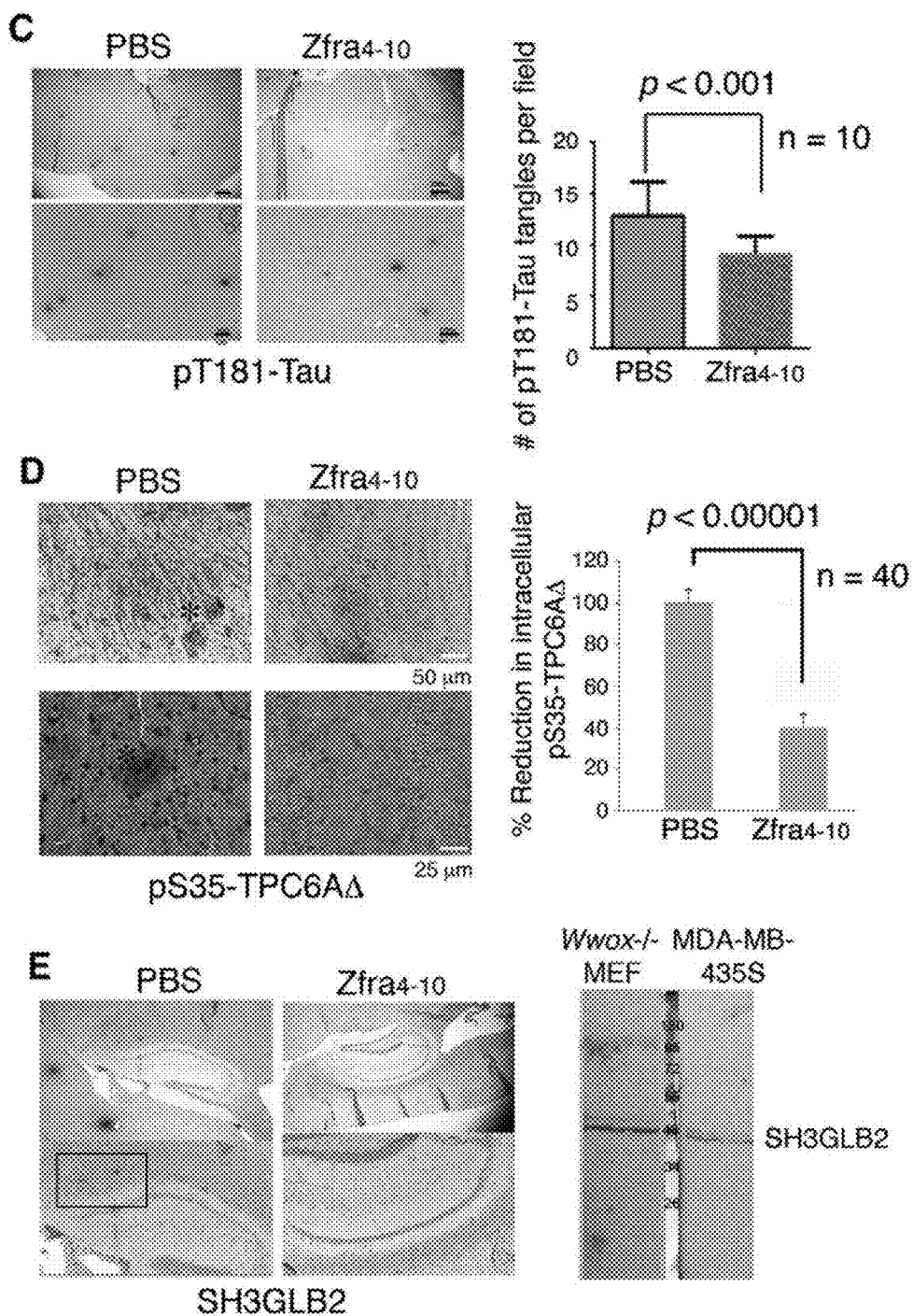

FIG. 3 includes photos and diagrams showing effect of Zfra on tau phosphorylation of the dorsal part hippocampi in 3×Tg mice. Representative micrographs of pS412-tau immunostaining are shown on the left panels, the boxed regions are enlarged and shown on the right, and the quantitative results are shown on the bottom. (A) Dorsal hippocampus. (B) Ventral hippocampus. *P<0.05 versus respective PBS group, two-tailed Mann-Whitney test. (C) Zfra inhibition of pT181-tau aggregation is shown (scale bar=200 μm for top panel and 100 μm for bottom panel). (D) Zfra suppressed intracellular pS35-TPC6AΔ expression (40 neurons counted) and extracellular pS35-TPC6AΔ plaque formation (see the blue asterisk). (E) Zfra blocked the aggregation of self-polymerizing SH3GLB2 (~70% suppression). The quality of homemade antibody is shown. Magnification: top panel 20× and bottom panel 100×. Abbreviations, Alv., alveus; S.L., stratum lacunosum; S.O., stratum oriens; S.P., stratum pyramidale; S.R., stratum radiatum.

Figure 4:
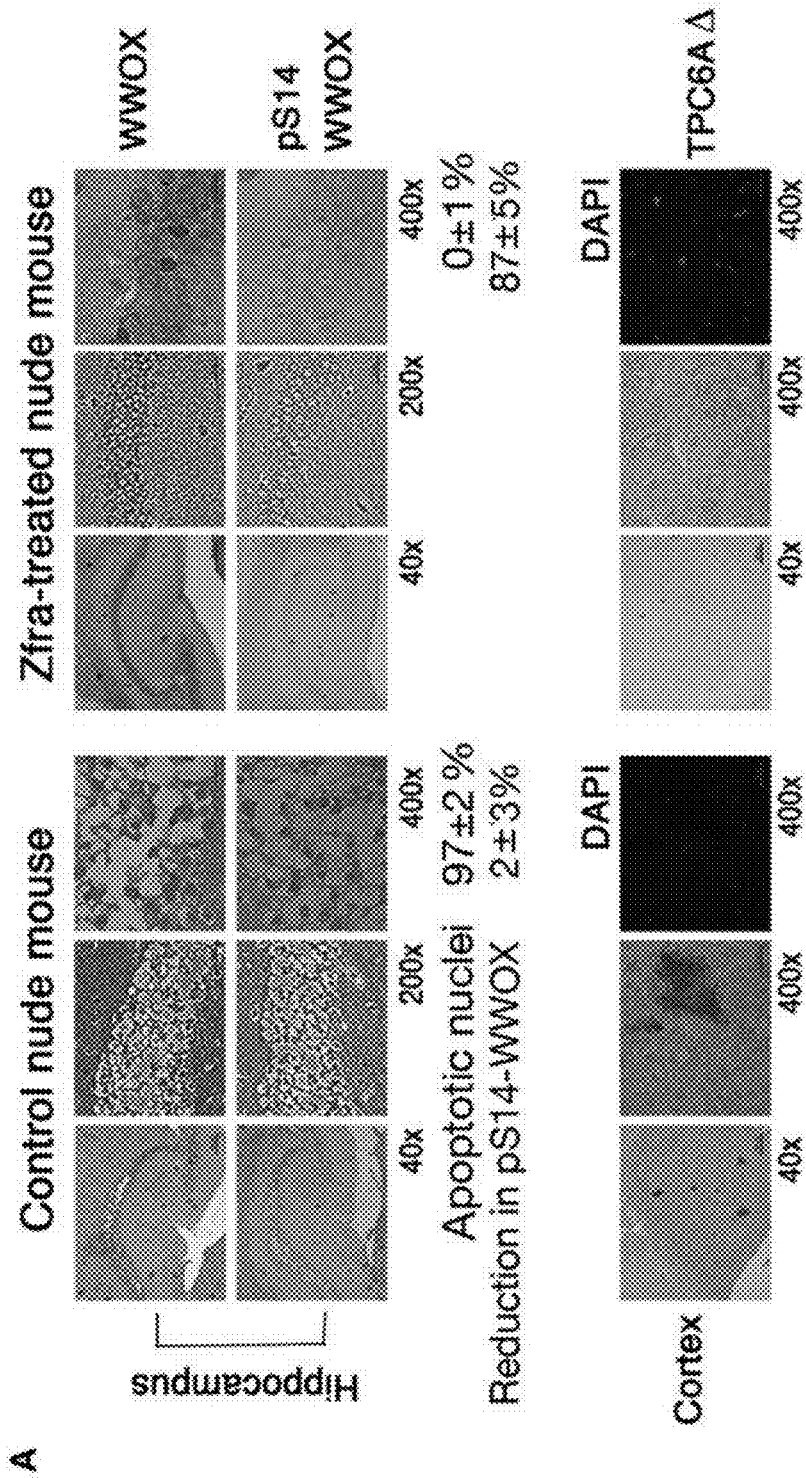
Figure 4:
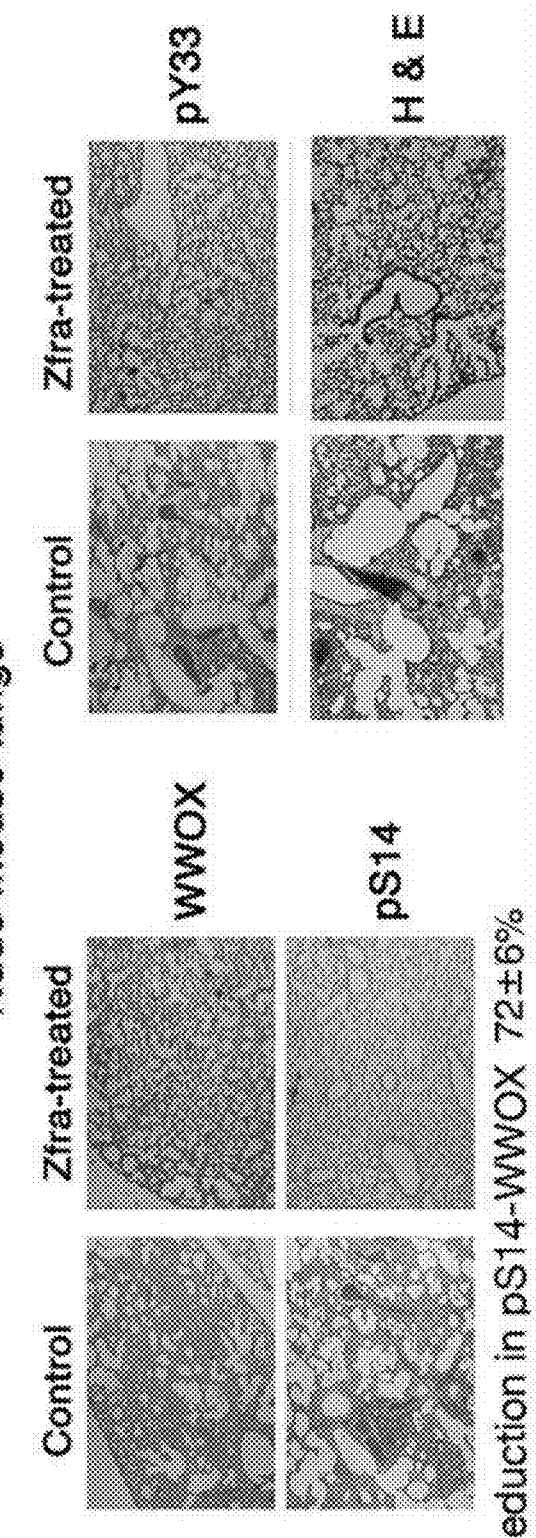
Figure 4:
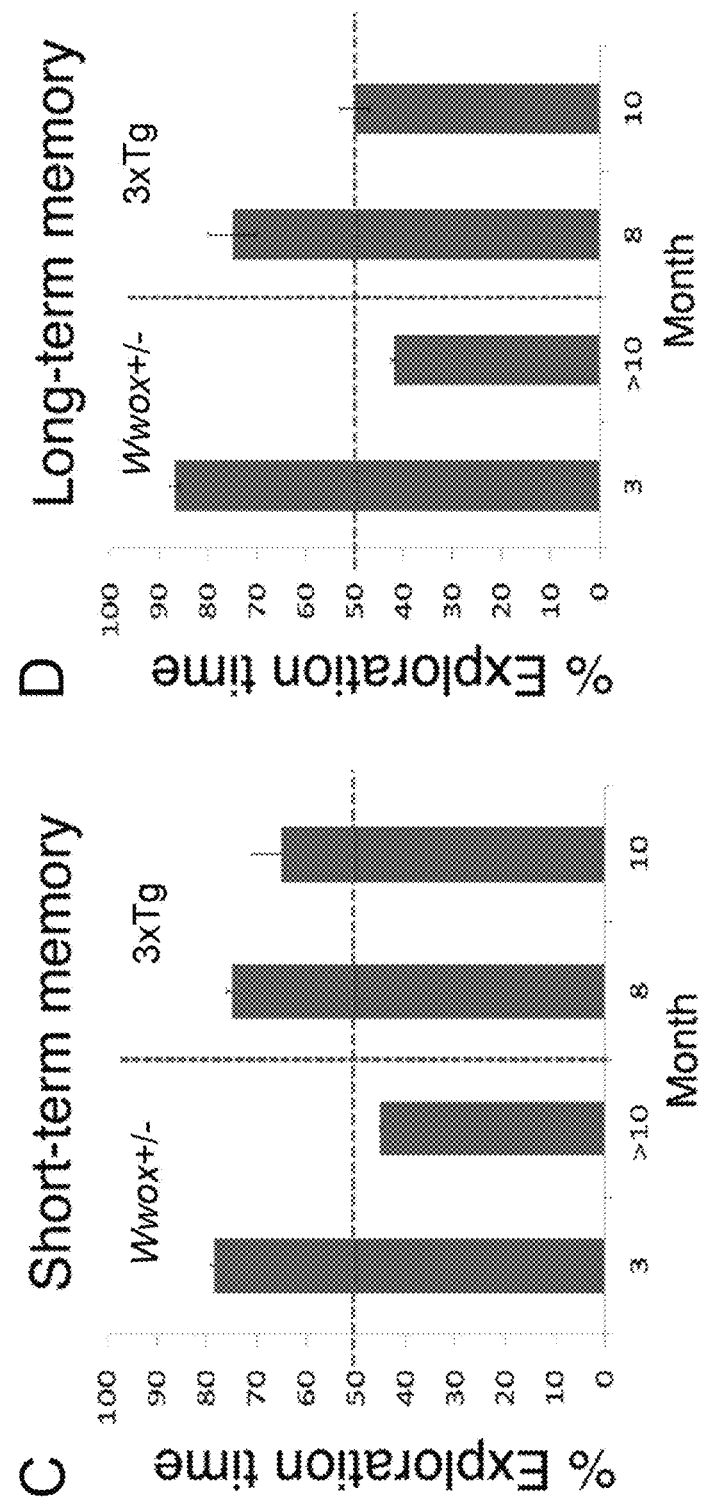

FIG. 4 includes photos showing that Zfra suppresses melanoma B16F10-mediated neurodegeneration in the hippocampus. Nude mice were preinjected with 100 μL, of sterile Milli-Q water or Zfra4-10 (1 mM in sterile water) in 3 consecutive weeks. After treatment for a week, these mice were inoculated with melanoma B16F10 cells on both flanks (2×10$^5$ cells in 100-μL, PBS). Mice were sacrificed when the tumor sizes grew up to 2000-3000 mm$^3$ in about a month. (A) Zfra blocked neurodegeneration in the hippocampus (top panel) and prevented the formation of TPC6AΔ plaques in the cortex (bottom panel), which negatively correlates with pS14-WWOX expression. Note the presence of condensed apoptotic nuclei in the hippocampal neurons in the control mice, (B) Metastasis of B16F10 cells to the lung was blocked in Zfra-treated mice. Compared to controls, Zfra suppressed p-S14WWOX expression in the lung by ~72% suppression (three sections). The WWOX protein levels were not suppressed. (C and D) The non-spatial learning and memory were determined by novel object recognition task for both 3×Tg and Wwox+/− mice. Both short-term and long-term memories for the Wwox+/− mice have dropped greater than 55% at ages 10-12 (n=5), whereas 3×Tg mice exhibited decline for less than 50%. Also, see data in FIG. 1.

Figure 5:
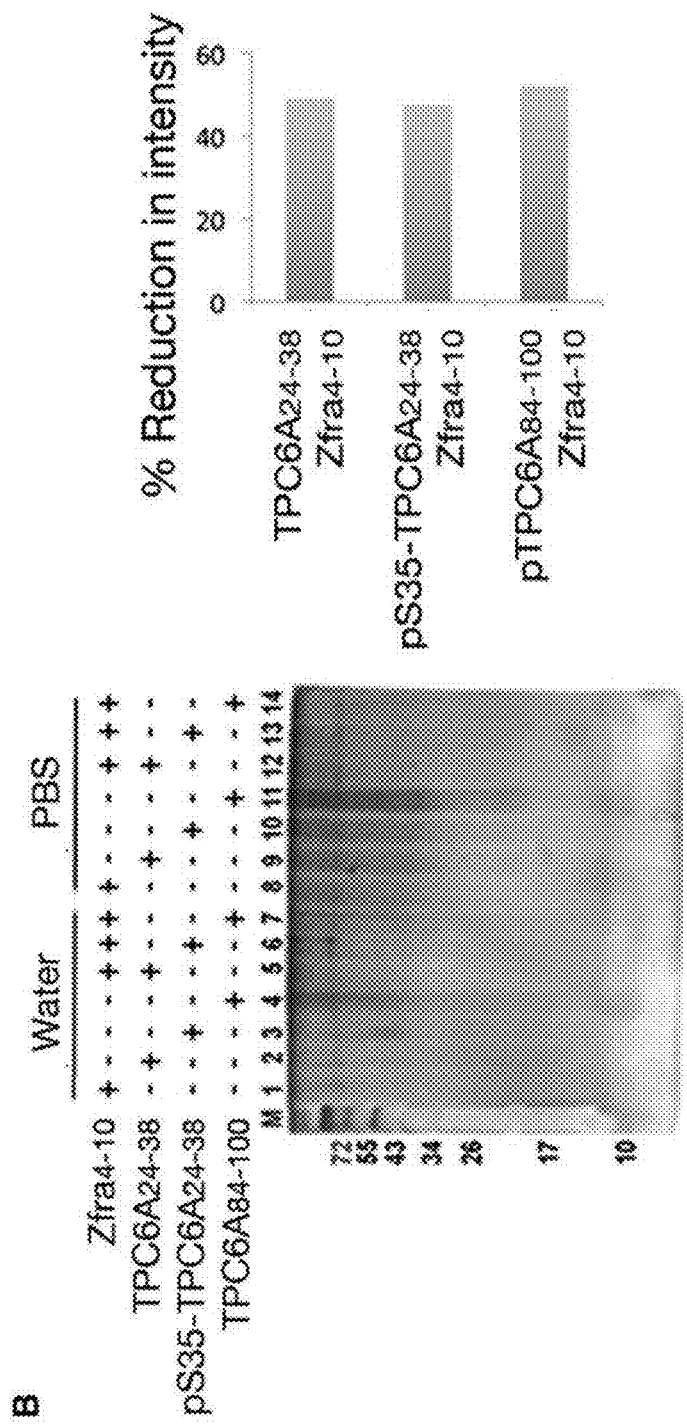
Figure 5:
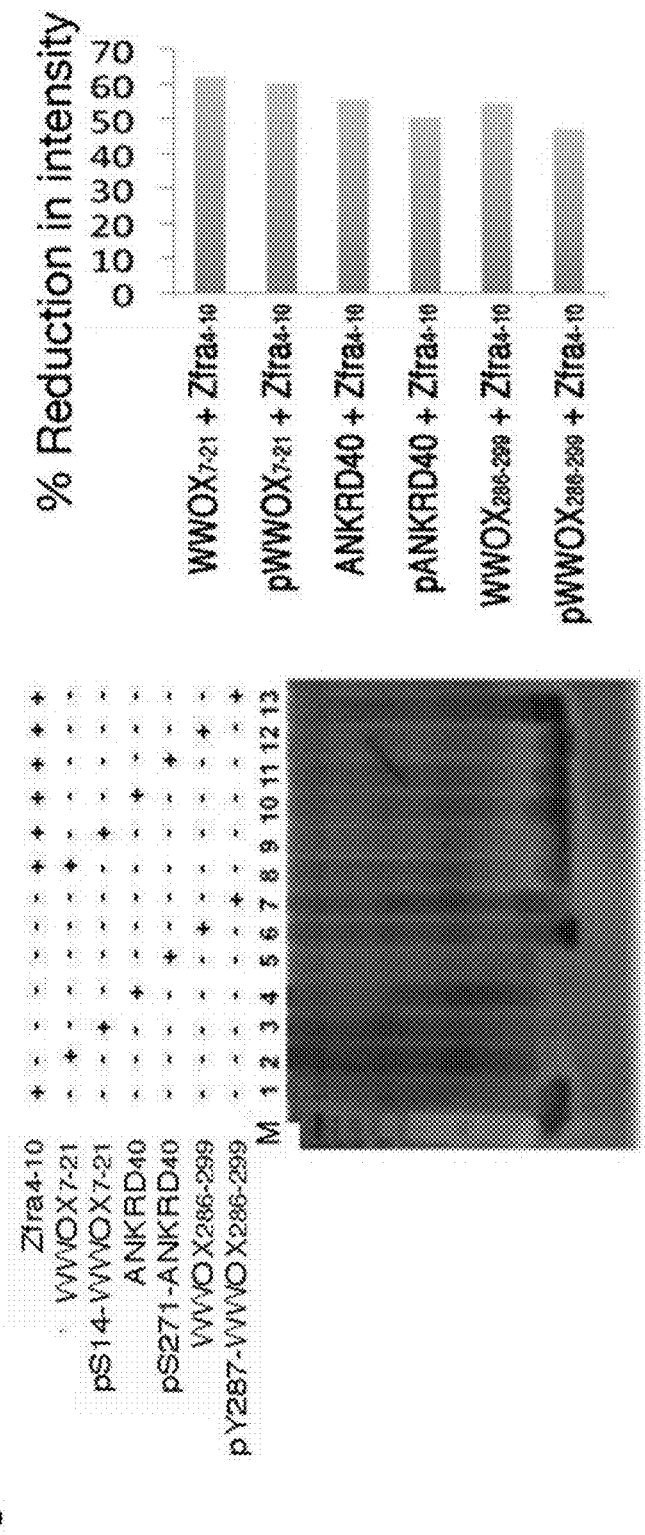

FIG. 5 includes photos and diagrams showing that Zfra suppresses polymerization or aggregation of serine-containing TPC6AΔ and other peptides in PBS. Zfra$_{4-10}$ was incubated with an indicated serine-containing peptide in PBS at room temperature for 24 hours (final 200 μM each peptide). The mixtures were subjected to nonreducing sodium dodecyl sulfate polyacrylamide gel electrophoresis (SDS-PAGE). (A) Full-length Zfra or red-fluorescent TMR-Zfra blocked aggregation of Aβ42 (lanes 3, 5, and 7). In controls, Aβ40 did not undergo aggregation. The membrane was stained with antibody against Aβ. (B) Zfra$_{4-10}$ and one of the TPC6AΔ peptides were resuspended in Milli-Q water or PBS and incubated for 24 hours at room temperature. Zfra$_{4-10}$ suppressed the polymerization of serine-containing peptides. Reduction in intensity=[1−(Z.P)/(Z+P)]×100%, where Z=Zfra$_{4-10}$, P=an indicated peptide, and Z.P=peptide mixture. (C) Under similar conditions, serine-containing peptides derived from WW OX and ANKRD40 were synthesized, possessing with or without phosphorylation at a specific serine or tyrosineresidue. Zfra$_{4-10}$ suppressed polymerization of these peptides in PBS.

Figure 6:
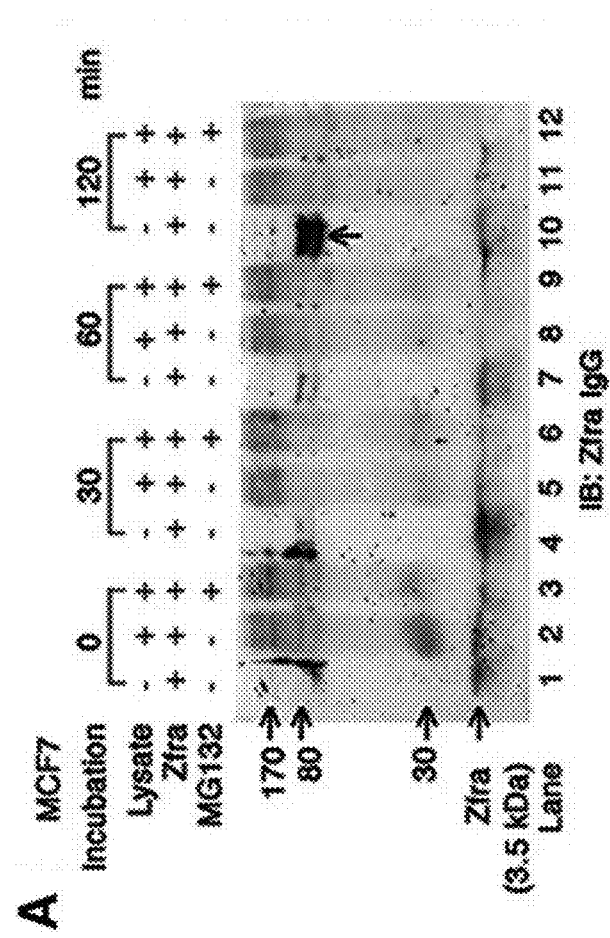
Figure 6:
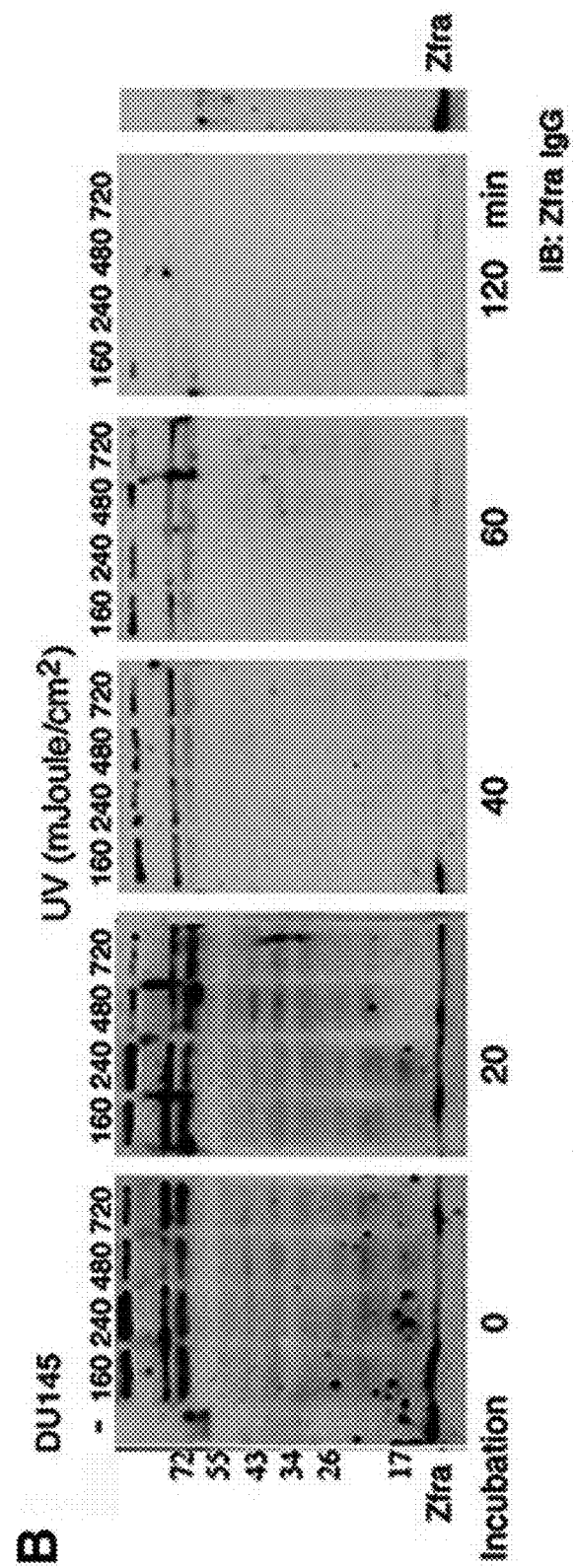
Figure 6:
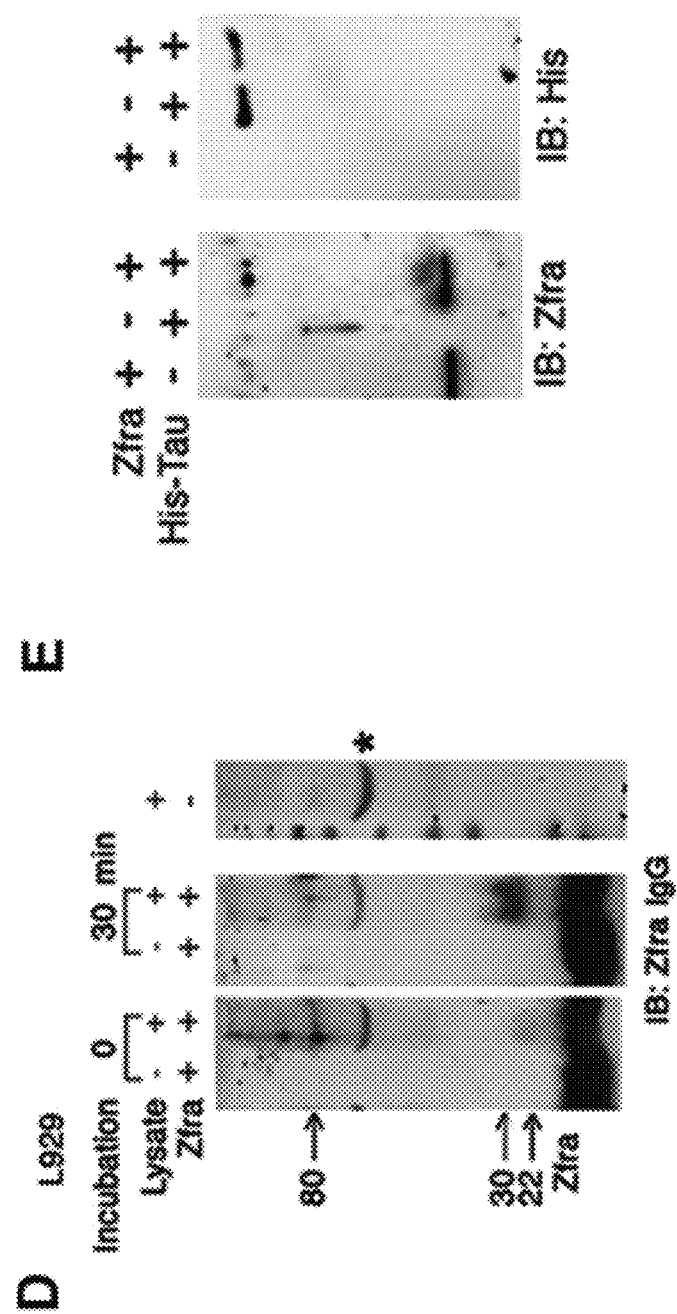

FIG. 6 includes photos and diagrams showing that Zfra covalently binds and accelerates protein degradation (A) On dissolving in PBS for 30-120 minutes at 37° C., Zfra peptide (3.5 kDa) underwent self-polymerization and formed large-size complexes (78 and 80 kDa), as determined by reducing SDS-PAGE and Western blotting (see the vertical arrow at lane 10, and lanes 1, 4, and 7). Aliquots of Zfra-deficient breast MCF7 cell lysates (100 μg) were incubated with Zfra (100 μM) for various durations in the presence or absence of proteasome inhibitor MG-132 (50 μM). Zfra formed complexes with cytosolic proteins (or zfrated; see arrows), and disappeared with time even in the presence of MG-132. (B and C) Zfra-negative prostate DU145 cells were exposed to UV (160-720 mJ/cm$^2$), and aliquots of whole cell lysates (100 μg) were incubated with Zfra peptide (100 μM) for various durations (in PBS) at 37° C., in the presence of a cocktail of protease inhibitors (1:10 dilution). Zfrated proteins (70, 72, 200 kDa and minor band ladders) and exogenous Zfra peptide were degraded with time (>99% in 120 minutes; reducing SDS-PAGE). Synthetic Zfra was in PBS at the first lane at the left, and in Milli-Q water at the last lane at the right. Zfra-free control lysates had only less than 10% degradation of total proteins after incubation for 120 minutes, in the presence of protease inhibitors (data not shown). In the diagram of FIG. 6C, at each time points, the left bar is cell lysates, and the right bar is Zfra peptide. (D) L929 cell lysates (100 μg) were incubated with Zfra peptide (100 μM) for 30 minutes at 37° C. (in PBS). A 30-kDa protein was zfrated in 30 minutes, and 22- and 80-kDa protein was zfrated rapidly and then degraded in 30 minutes (reducing SDS-PAGE). *A nonspecific immunoreactive or a zfrated protein in L929 cells. (E) Zfra peptide (100 μM) bound recombinant His-Tau (2 μg protein) in PBS for 24 hours at room temperature, and the resulting complex resisted dissociation by reducing SDS-PAGE. Abbreviation: Zfra, zinc finger-like protein that regulates apoptosis.

Figure 7:
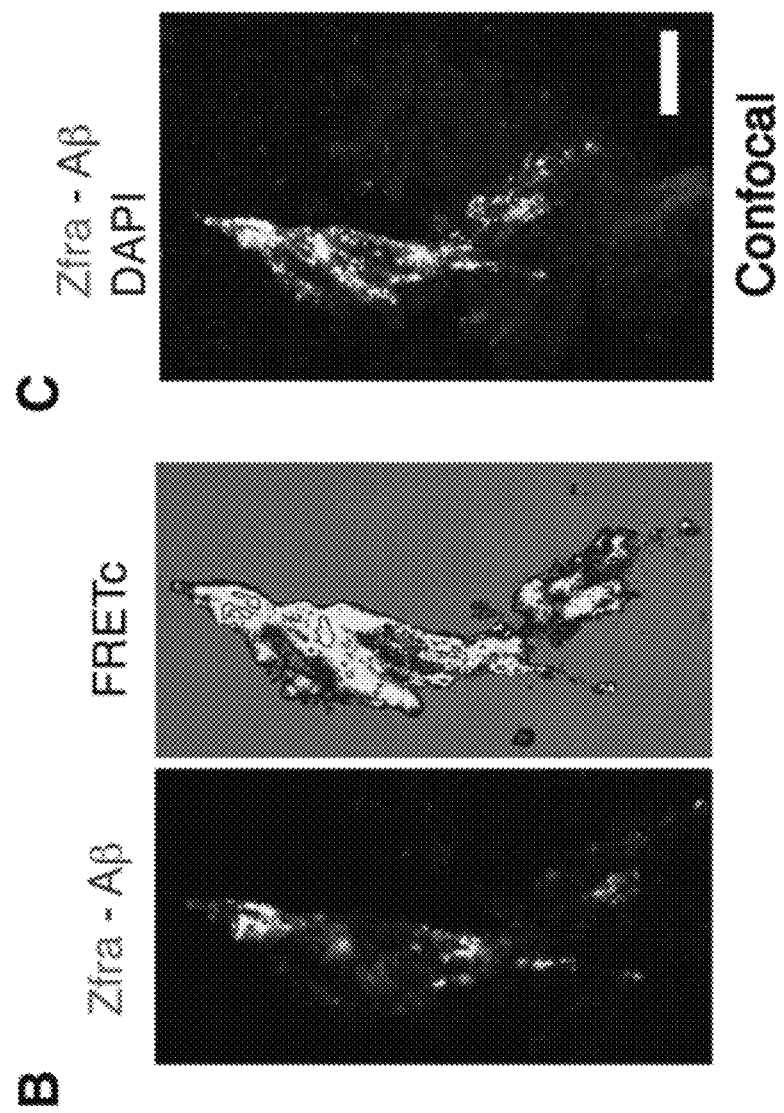
Figure 7:
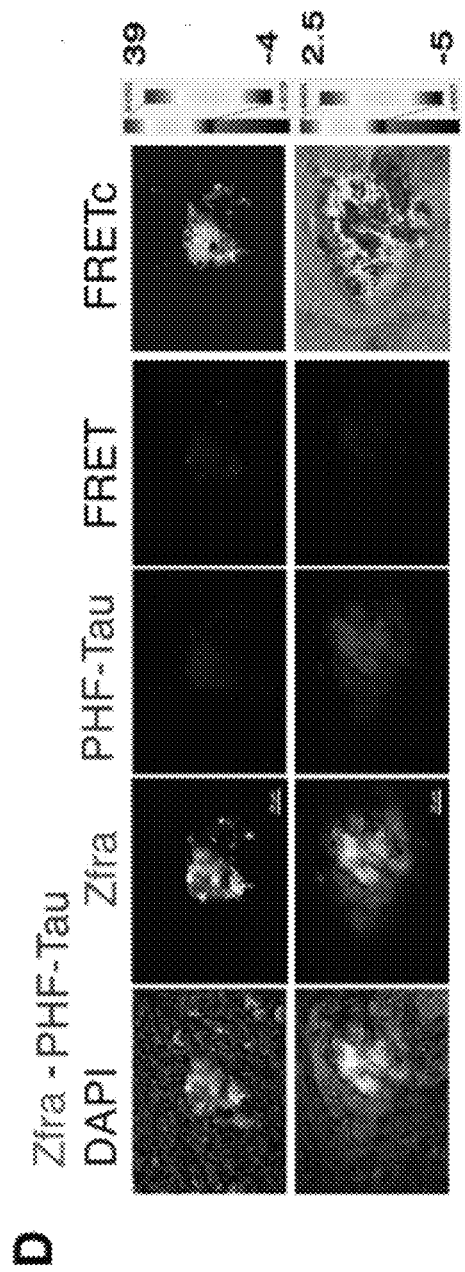
Figure 7:
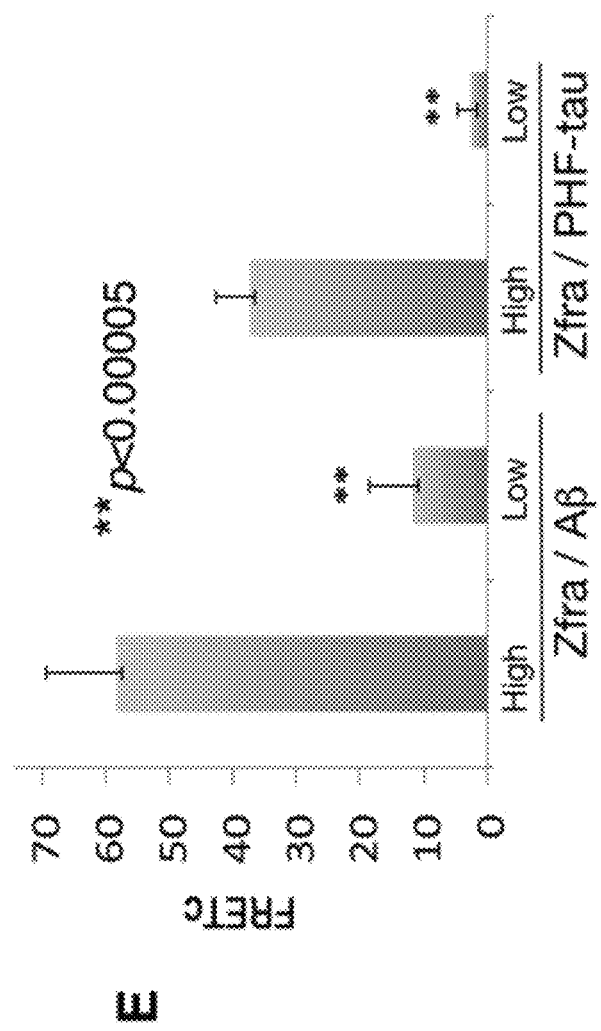
Figure 7:
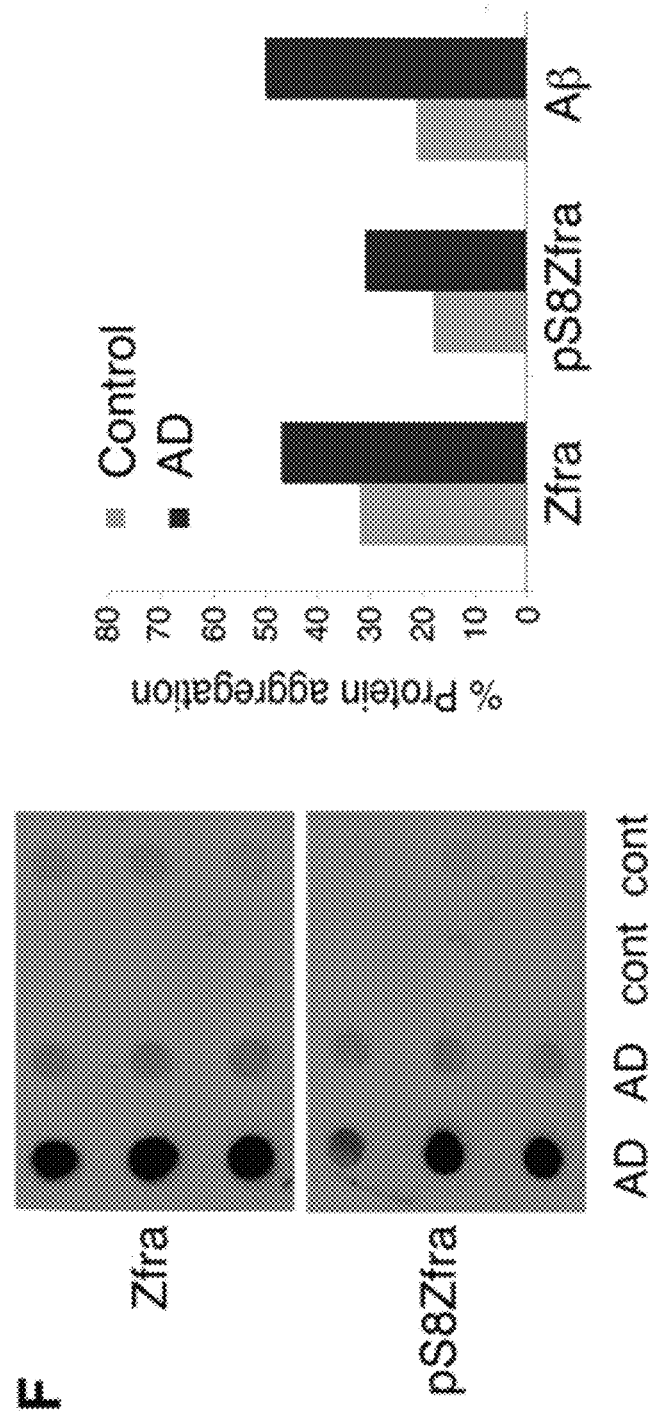
Figure 7:
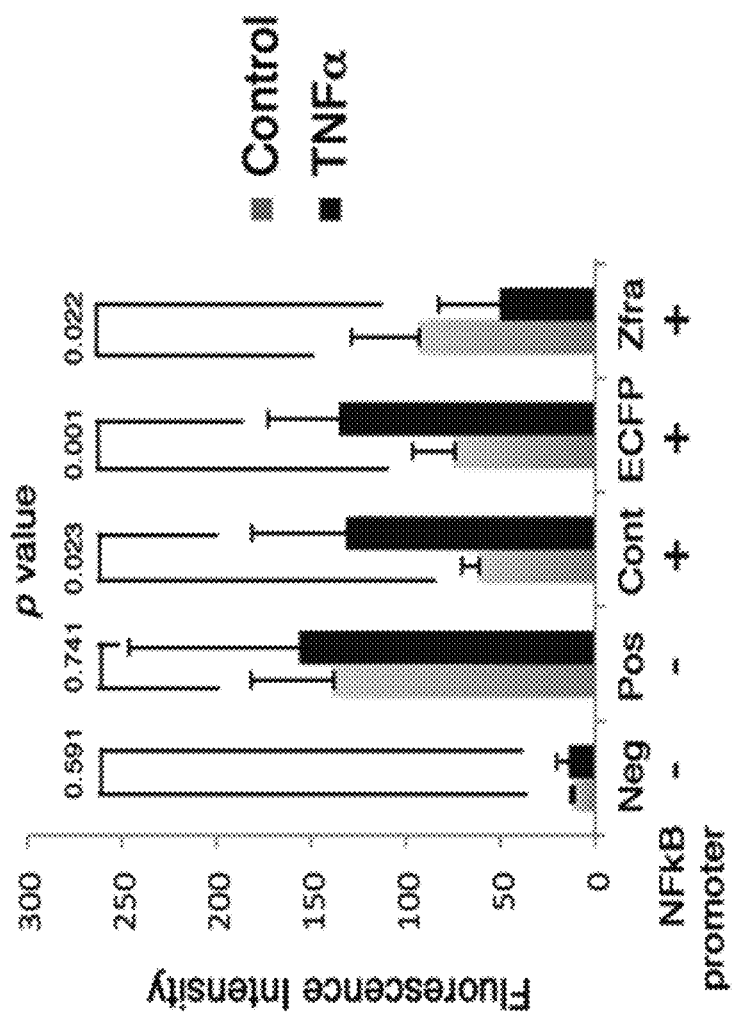

FIG. 7 includes photos and diagrams showing that Zfra is upregulated in the AD hippocampi and interacts with tau and Aβ and blocks NF-κB promoter activation. (A and B) By antibody FRET microscopy, Zfra bound Aβ with a high affinity (FRETc greater than 45) in the hippocampal sections of postmortem AD patients (see yellow punctates in B). However, Zfra may colocalize with Aβ but without binding (FRETc less than 5). (C) Confocal microscopy analysis revealed the colocalization of Zfra with Aβ. (D) Zfra binds PHF-tau with a similar pattern. (E) A bar graph of Zfra binding with Aβ or PHF-tau is shown (n=20). (F) By filter retardation assay using insoluble human hippocampal extracts, aggregation of Zfra and pSer8-Zfra was increased by 45 and 85%, respectively, in the older AD patients (81±9.7 years old; n=70), compared to younger nondemented controls (60±13.3 years old; n=46). Aβ was increased by 170% in the AD patients. In this diagram, the left bar is control and the right bar is AD. (G) Zfra significantly blocked TNF-α (50 ng/mL)-mediated activation of NF-κB promoter in COST cells. In this diagram, the left bar is control and the right bar is INF-α. Abbreviations, Neg, negative control; PHF, paired helical filament; Pos, positive control.

Figure 8:
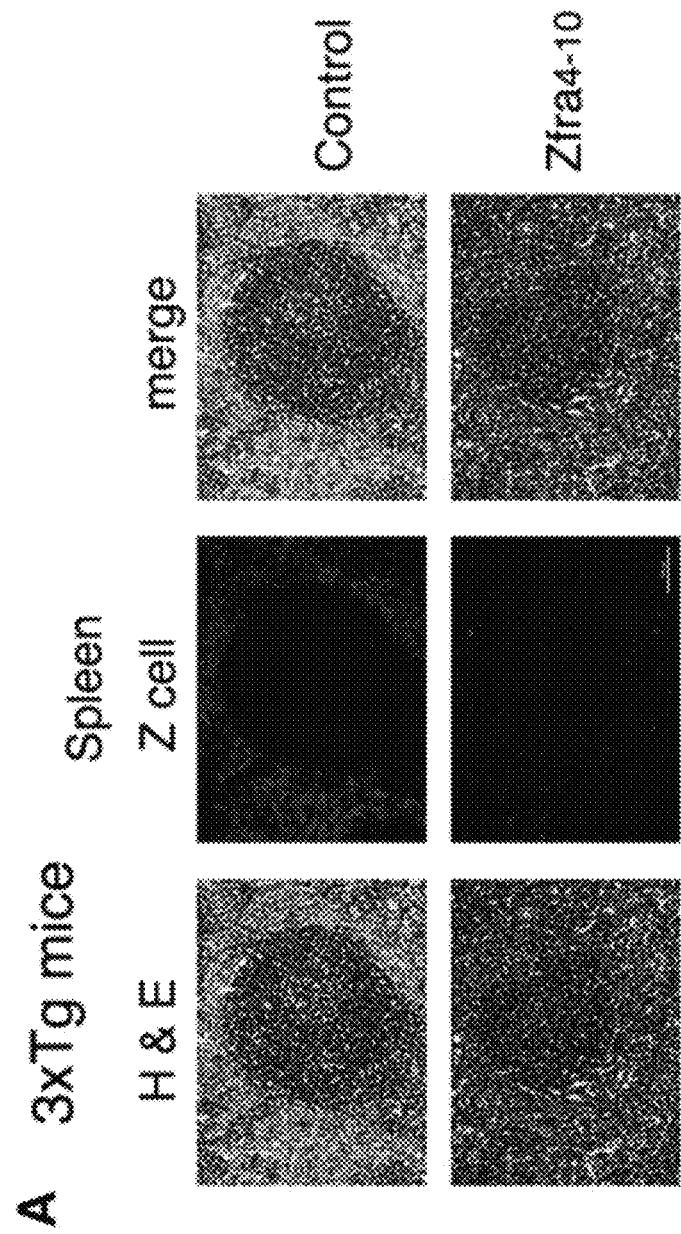
Figure 8:
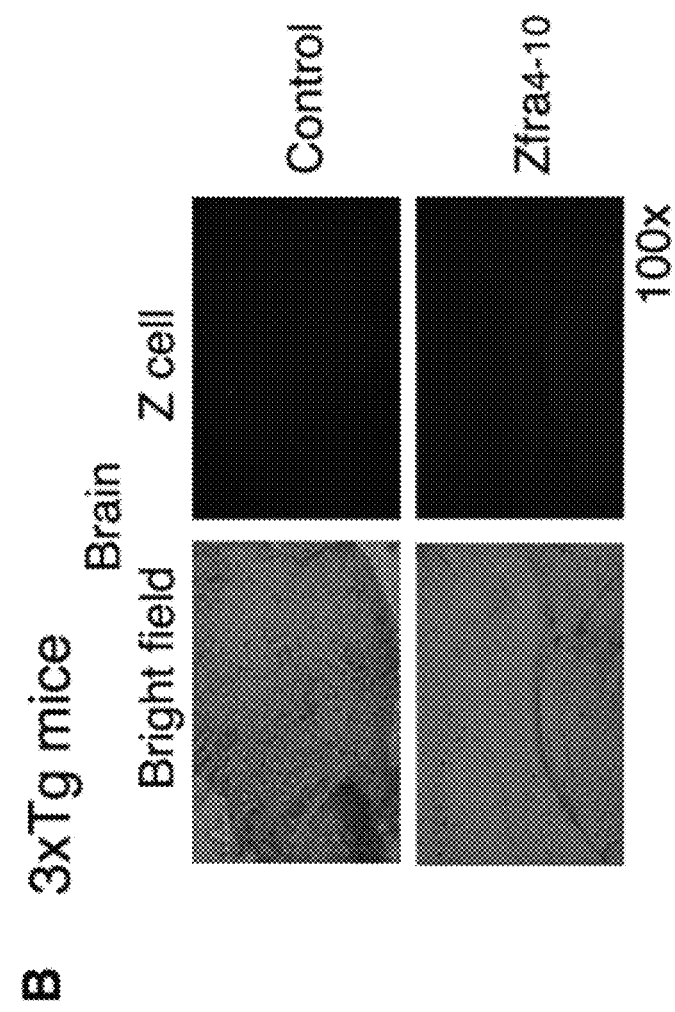
Figure 8:
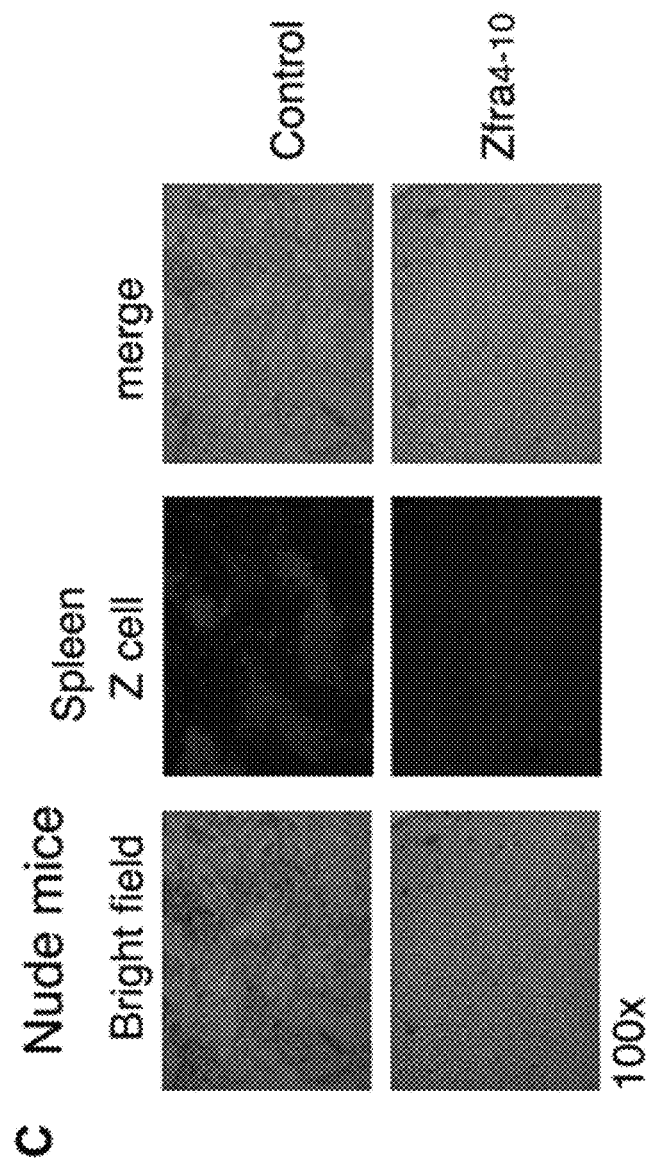
Figure 8:
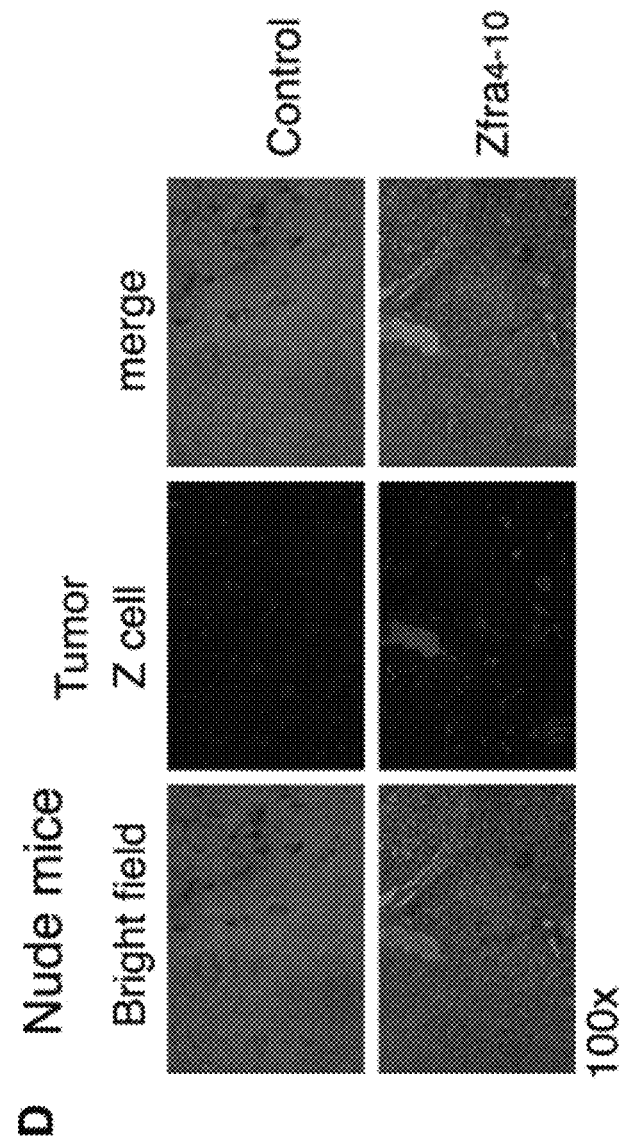

FIG. 8 includes photos showing that Zfra induces spleen Z cells to relocate out of the spleen, but the cells do not appear to migrate to the brain. (A) Spleen sections from Zfra-treated and control 3×Tg mice were stained with TMR-Zfra, followed by determining the presence of Z cells by fluorescence microscopy. Z-cell migration out of the spleen is shown in the Zfra-treated 3×Tg mice. Scale bar is 100 μm in length (100× magnification). (B) Similar experiments were carried out using brain tissue sections of 3×Tg mice. Brain sections were examined. (C and D) Similarly, spleens were harvested from Zfra-treated and control nude mice, which were inoculated with melanoma B16F10. Zfra induced Z-cell relocation out of the spleen, and the cells were found in the skin cancer lesions. Abbreviations, TMR-Zfra, tetramethylrhodamine-labeled. Zfra.

DETAILED DESCRIPTION

The present disclosure is based on the unexpected discoveries that the zinc-finger like peptide, either in a truncated form or full-length, can downregulating protein (such as TRAPPC6AΔ, SH3GLB2, tau, or Aβ aggregation) aggregation in brain, wherein the protein aggregation may result in plaque formation, which is one factor causing neurodegenerative disease. Thus, the zinc-finger like peptide, either in a truncated form or full-length, has the potential on treating neurodegenerative disease such as Alzheimer's disease.

Accordingly, the present disclosure provides a method for downregulating protein aggregation in brain, comprising: administering an effective amount of a zinc finger-like peptide to a subject in need thereof, wherein the zinc finger-like peptide comprises an amino acid sequence of

RRSSSCK.   (SEQ ID NO: 1)

The present disclosure also provides a method for treating Alzheimer's disease, comprising: administering an effective amount of a zinc finger-like peptide to a subject in need thereof, wherein the zinc finger-like peptide comprises an amino acid sequence of RRSSSCK (SEQ ID NO: 1).

Also within the scope of the present disclosure are a pharmaceutical composition for downregulating protein aggregation in brain or for treating Alzheimer's disease, comprising the zinc finger-like peptide; and use of the zinc finger-like peptide for manufacturing a medicament for downregulating protein aggregation in brain or for treating Alzheimer's disease.

In the present disclosure, the zinc-finger like protein that regulates apoptosis (Zfra) is a 31-amino-acid peptide containing two cysteines and one histidine and is similar to C2H2-type zinc finger proteins. The amino acid sequence of the full-length Zfra is:

NH-MSSRRSSSCKYCEQDFRAHTQKNAATPFLAN-COOH   (SEQ ID NO: 2)

The serine residue with underline is the serine phosphorylation sites Serb (S8), which is essential to the activity of Zfra in regulating apoptosis. The term "Zfra peptide" used in the present disclosure refers to a peptide comprising the amino acid sequence of SEQ ID NO: 1 (Zfra$_{4-10}$). A Zfra peptide may consist of up to 50 amino acid residues (e.g., up to 45, 40, 35, 30, 25, or 20 amino acid residues). In some examples, a Zfra peptide as described herein may comprise SEQ ID NO: 1 and share at least 75% sequence identity (e.g., 80%, 85%, 90%, 95%, or higher) as compared with the full-length Zfra (SEQ ID NO: 2). In one example, the Zfra peptide consists of SEQ ID NO: 2.

The "percent identity" of two amino acid sequences is determined using the algorithm of Karlin and Altschul Proc. Natl. Acad. Sci. USA 87:2264-68, 1990, modified as in Karlin and Altschul. Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g.,)(BLAST and NBLAST) can be used.

The sequence of the zinc finger-like peptide can be derived from any zinc finger-like peptide of different species. For example, the zinc finger-like peptide is derived from human or mouse. In addition, the zinc finger-like peptide may be obtained through peptide synthesis, or expression of cDNA of zinc finger-like peptide from human or mouse. For example, the zinc finger-like peptide of the present disclosure is obtained through peptide synthesis.

The zinc finger-like peptide of the present disclosure has similar structure to zinc-finger motif. In addition, the peptide of the present disclosure may selectively contain several duplicate amino acid residues with similar chemical properties or several duplicate identical amino acid residues to form a peptide motif with specific bonding. Furthermore, the zinc finger-like peptide can self-polymerize without adding any catalytic agents. The zinc finger-like peptide of the present invention also can bind to proteins related to apoptosis.

The zinc finger-like peptide and the pharmaceutical composition of the present invention can be administered via parenteral, inhalation, local, rectal, nasal, sublingual, or vaginal delivery, or implanted reservoir. Herein, the term "parenteral delivery" includes subcutaneous, intradermic, intravenous, intra-articular, intra-arterial, synovial, intrapleural, intrathecal, local, and intracranial injections.

In the pharmaceutical composition of the present disclosure, the term "pharmaceutically acceptable carrier" means that the carrier must be compatible with the active ingredients (and preferably, capable of stabilizing the active ingredients) and not be deleterious to the subject to be treated. The carrier may be at least one selected from the group consisting of active agents, adjuvants, dispersants, wetting agents and suspending agents. The example of the carrier may be microcrystalline cellulose, mannitol, glucose, non-fat milk powder, polyethylene, polyvinylpyrrolidone, starch or a combination thereof.

In addition, the term "treating" used in the present disclosure refers to the application or administration of the zinc finger-like peptide or the pharmaceutical composition containing the zinc finger-like peptide to a subject with symptoms or tendencies of suffering from, for example, Alzheimer's disease, in order to cure, heal, alleviate, relieve, alter, remedy, ameliorate, improve, prevent or affect the symptoms or tendencies of cancers. Furthermore, "an effective amount" used herein refers to the amount of each active ingredients such as the zinc finger-like peptide required to confer therapeutic effect on the subject. The effective amount may vary according to the route of administration, excipient usage, and co-usage with other active ingredients.

In one aspect of the present disclosure, the zinc finger-like peptide can be co-administered with one or more agent which is capable of downregulating protein (such as TRAPPC6AΔ, SH3GLB2, tau, or Aβ) aggregation or for treating Alzheimer's disease.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Embodiment

Methods

Peptides

Zfra and serine-containing peptides were synthesized by Genemed Synthesis (San Antonio, Tex., USA), (1) Zfra$_{1-31}$, MSSRRSSSCKYCEQDFRAHTQKNAAFPFLAN (SEQ ID NO: 2); (2) Zfra$_{4-10}$, RRSSSCK (SEQ ID NO: 1); (3) WWOX$_{7-21}$, AGLDDTDSEDELPPG (SEQ ID NO: 3); (4) pS14-WWOX$_{7-21}$, AGLDDTDpSEDELPPG (SEQ ID NO: 4); (5). WWOX$_{286-299}$, DYWAMLAYNRSKLC (SEQ ID NO: 5); (6) pY287-WWOX$_{286-299}$, DpYWAMLAYNRSKLC (SEQ ID NO: 6); (7) TPC6A$_{24-38}$, DPGPGGQKMSLSVLE (SEQ ID NO: 7); (8) pS35-TPC6A$_{24-38}$, DPGPGGQKMSLpSVLE (SEQ ID NO: 8); (9) TPC6A$_{84-100}$, KDLWVAVFQKQMDSLR (SEQ ID NO: 9); (10) ANKRD40$_{266-281}$, RIQNPSLRENDFIEIE (SEQ ID NO: 10); (11) pS271-ANKRD40$_{266-281}$, RIQNPpSLRENDFIEIE (SEQ ID NO: 11); (12) tetramethylrhodamine-labeled Zfra (TMR-Zfra), the full-length Zfra$_{1-31}$ was labeled with a red-fluorescent Texas Red maleimide fluorescent probe tetramethylrhodamine. The peptide stocks were made as 10 mM in degassed sterile Milli-Q water. Each tube was flushed with nitrogen and stored in −80° C. freezer. For tail vein injections, peptides were freshly prepared in degassed Milli-Q water at 1-4 mM in 100-µL Milli-Q. GenBank accession for ANKRD40 is EU164539. Aβ peptides were from AnaSpec, (1) Aβ42: DAEFRIIDSGYEVHHQKLVFFAEDVGSNKGAIIGLMVGGVVIA (SEQ ID NO: 12); (2) Aβ40: DAEFRHDSGYEVHHQKLVFFAEDVGSNKGAIIGLMVGGVV (SEQ ID NO: 13). Where indicated, Zfra peptide was mixed and incubated with an aforementioned peptide for 12-24 hours at room temperature, followed by determining peptide aggregation using sodium dodecyl sulfate polyacrylamide gel electrophoresis (SDS-PAGE) and silver staining.

Antibodies

Homemade antibodies used in the experiments were against Zfra, pS8-Zfra, and WWOX (WOX1). Commercial antibodies used were as follows: (1) monoclonal Aβ antibody (AbD/Serotec), (2) monoclonal paired helical filament (PHF)-tau antibody (Pierce/Invitrogen), (3) EGFP (Santa Cruz Laboratory), (4) His tag antibody (Sigma), (5) pT181-tau antibody (Biosource). An approved protocol for rabbit use in antibody production was from the IACUC of the National Cheng Kung University Medical College. Antibodies were produced using the following synthetic peptides, (1) WWOX$_{7-21}$, CAGLDDTDSEDELPPG (SEQ ID NO: 14); (2) pS14-WWOX$_{7-21}$, CAGLDDTDpSEDELPPG (SEQ ID NO: 15); (3) TPC6A, CKDLWVAVFQKQMDSLR (SEQ ID NO: 16), amino acid #84-100 for pan-specific antibody production. These peptides were conjugated with keyhole limpet hemocyanin (KLH) via the N-terminal cysteine for antibody production in rabbits (using an Antibody Production and Purification kit from Pierce). The N-terminal cysteine in each peptide sequence was added for covalently conjugating with KLH. The specific pS14-WWOX antibody was purified. The specificity of the antisera was tested using the synthetic peptides to block immunoblots. Where indicated, Western blotting was carried out. In addition, we generated antibody against self-polymerizing SH3GLB2 (SH3 domain-containing GRB2-like endophilin B2), using the synthetic peptide (amino acid 170-185)
(SEQ ID NO: 17)
NH-CDACKARLARLKKAKAAEAK-COOH.

Animals

All experiments were carried out in accordance with the National Institutes of Health Guidelines for animal research (Guide for the Care and Use of Laboratory Animal) and approved by the National Cheng Kung University Institutional Animal Care and Use Committee. The 3×Tg mice (B6; 129-Psen1tm1Mpm Tg[APPSwe, tauP301L]1Lfa/Mmjax), were obtained from the Jackson Laboratory (Bar Harbor, MB, USA) and housed in a controlled room (temperature 23±1° C., humidity 55±5%, 12-hour light/12-hour dark cycle, light cycle begins at 06:00) located in the Laboratory Animal Center of National Cheng Kung University (Tainan, Taiwan) with unrestricted access to food and water. All mice were genotyped using a protocol provided by the Jackson Laboratory. The 3×Tg mice develop intracellular Aβ immuno-positive staining as early as 3-4 months and aggregates of hyperphosphorylated tau in the hippocampus around 12 months of age. Impaired synaptic transmission and long-term potentiation are evident about 6 months of age. At the age of 10 months (body weight, 31~35 g), five 3×Tg mice received four consecutive weekly injections of Zfra4-10 solution (2 mM in phosphate buffered saline [PBS], 100 µL each injection) from the tail veins. Another five mice underwent the same procedure with PBS injections served as a sham control group. After necessary behavioral tests shown in the following, mice were sacrificed by $CO_2$ anesthesia (75% $CO_2$/25% $O_2$) and perfused with 10-mL PBS (to reduce background in tissue section staining with specific antibodies). Brains were then rapidly harvested.

Novel Object Recognition Test

The experiment was performed from 6 PM each day. One week after the last injection of Zfra$_{4-10}$ solution, mouse was habituated to a polycarbonate box (47.5 cm×25.8 cm×21 cm) for 10 minutes per day for 3 consecutive days. On the next day each mouse was placed back into the same box containing two identical objects (glass bottle, 4-cm diameter and 6.5-cm high) separately positioned 7 cm away from a wall. The cumulative times spent by the mouse in exploring each of the objects were recorded during a 5-minute period. Two hours later, the mouse was reintroduced into the box for the short-term memory (STM) test. One of the two objects was replaced by a new one (white Lego bricks, 3 cm×3 cm×6 cm). For the long-term memory (LTM) test, the mouse was reintroduced into the box after 24 hours. One of the two objects was replaced by a new one (white plastic bottle, 3.5 cm diameter and 7.2 cm high). The times spent in exploring each object during a 5-minute period were recorded in either the STM or the LTM test. All of the objects were cleaned by 70% alcohol between trials to reduce olfactory cues.

Morris Water Maze Test

The hippocampus-dependent spatial learning and memory was evaluated by Morris water maze test, 1 day after the completion of novel object recognition test. The Morris water maze was performed in a custom-made circular pool with a diameter of 120 cm and a wall height of 31 cm, which was filled with clear tap water at a temperature of 24±1° C. and depth of 25 cm. The circular escape platform made of transparent Plexiglas (diameter 10 cm) was submerged 1 cm below the surface of the water. During all trials of spatial navigation, the location of the hidden platform was kept constant. Animals were given a one-session training, began at 18:00, per day for 4 days. Each session consisted of four swim trials (maximum 120 seconds per trial) with different quadrant starting positions for each trial. On the fifth day morning, animals were subjected to probe test. During the probe test, mouse was placed in the pool in the southwest position, the longest distance from the previous platform position (northeast), and the mouse was allowed to swim for 60 seconds without platform present. The whole process was recorded by a CCD camera, and the escape latency (i.e., time to reach the platform, in seconds), path length, and swim speed (cm/s) were analyzed by EthoVision video tracking system (Noldus Information Technology, Wageningen, Netherlands).

Brain Processing and Immunohistochemistry

After removing the brains, the right hemispheres were stored at −70° C., whereas the left hemispheres were fixed in 4% buffered paraformaldehyde at 4° C. ready for frozen sections. Coronal sections (30-μm thickness) of the right hemisphere were collected in cryoprotectant solution (30% ethylene glycol, 20% glycerol, 50-mM sodium phosphate buffer, pH 7.4) and stored at −20° C. The brain sections were washed, blocked with goat serum (3% in PBS/0.5% Triton X-100) for 1 hour, and probed with the following primary antibodies, pS412-tau (1:1000, AS-55418P, Anaspec, Fremont, Calif., USA) and a mixture of 6E10 (1:1000, against Aβ 1-17, Signet, Dedham, Mass., USA) and 4G8 (1:1000, against Aβ 17-24, Signet). The floating sections were incubated in primary antibodies for 16 hours at 4° C., then incubated with appropriate secondary antibodies (1:1000, Vector Laboratories, Burlingame, Calif., USA) and an avidin-biotin peroxidase (Vector) using 3, 3'-diaminobenzidine as the substrate. A parallel section stained without primary antibody served as negative control.

For the Aβ-positive cell counting, two sections, representing dorsal hippocampus (stereotaxic reference, bregma −2.2±0.2 mm) and ventral hippocampus (stereotaxic reference, bregma −3.3±0.2 mm), were selected. Only those cells with Aβ immunostaining signal intensity higher than a given background threshold, determined by the ImagePro plus 6.0 software (Bethesda, Md., USA), and with clear and identifiable cell bodies were counted. The background intensity threshold was fixed and applied to all sections.

To analyze pS412-tau signals, photomicrographs were taken from dorsal and ventral hippocampus using an AxiocamMRc digital camera connected to a computer equipped with Axiovision 4.8 software (Carl Zeiss, Oberkochen, Germany). The intensity of pS412-Tau immunoreactivity was evaluated by means of a relative optical density (ROD), which was obtained after transforming the RGB format to gray-scale format. ROD of the background was determined in unlabeled portions using ImagePro plus 6.0 software (Bethesda, Md., USA), and the value was subtracted for correction. The background intensity threshold was fixed and applied to all sections.

Thioflavin-S Staining

The mounted slice was incubated with 0.2% (w/v) thioflavin-S in PBS for 30 minutes to stain for matured (β-pleated sheet-containing) amyloid plaques. After washing the tissue three times with PBS, the slice was dehydrated in sequence with 50%, 75%, 95%, and 100% ethanol. After dehydration, the slice was submerged in Xylene for 10 minutes and attached to glass slide with mounting gel.

Statistical Analysis

All experimental results were represented as mean±standard error of the mean. The results for novel object recognition test, probe test of Morris water maze, relative ventricle area, and relative optical density of pS412-tau immunoreactivity were analyzed by two-tailed Mann-Whitney test, whereas the Aβ-positive cell number was analyzed by two-tailed unpaired t-test. The Morris water maze learning section results were analyzed using a repeated mixed-model analysis of variance with training session as within-subject factor and the Zfra injection as between-subject factor. Bonferroni post hoc tests were performed if significant ($P<0.05$) main effects were found.

Neurodegeneration Model in Tumor-Growing Mice

Six- to eight-week-old male nude (BALB/cAnN.Cg-Foxn1$^{nu}$/CrlNarl) mice (National Laboratory Animal Center, Taiwan) were used. Mice were intravenously injected into tail veins with 100 μL of Zfra$_{1-31}$ or Zfra$_{4-10}$ (2 mM), or sterile water. After injection for 1-8 weeks, mouse melanoma B16F10 or human glioma 13-06-MG cells ($2-2.5 \times 10^6$ cells/100-μL saline) were then inoculated in subcutaneous sites at both flanks. Tumor volumes were measured daily and calculated using the equation, $D \times (d)^2/2$, where D and d are the major and minor diameters, respectively. At indicated time point, mouse organs, including brain, lung, spleen, and liver, were harvested and fixed with 4% paraformaldehyde. IHC was carried out using indicated specific antibodies to determine protein expression in tissues and organs. Where indicated, TMR-Zfra was used to stain spleen, brain, and lung tissues. Z-cell distribution in organs was determined under fluorescence microscopy.

Human Hippocampal Tissues, Tissue Extractions for Filter Retardation Assay, and Tissue Sections for Immunohistochemistry We obtained human postmortem frozen hippocampal tissues and fixed-tissue sections from hippocampi from the Brain Bank of the Department of Pathology, University of Colorado Health Sciences Center (by Dr. CI Sze, before 2005). Institutional review board approval was waived. Informed consents were obtained from the family members of the deceased patients. Where indicated, the tissue samples were homogenized in a lysis buffer and the insoluble fractions subjected to filter retardation assay. Presence of Zfra, pS8Zfra, and Aβ was determined by using specific antibodies in dot blotting and quantified.

Promoter Activation Assay

We examined whether Zfra affected tumor necrosis factor (TNF)-mediated activation of promoter governed by NF-κB. COST cells were transfected with a promoter construct for NF-κB using green fluorescent protein (GFP) as a reporter by electroporation, followed by exposure to TNF (50 ng/mL) for 24 hours. Both positive and negative controls were also tested in each experiment.

Results

Figure 1:
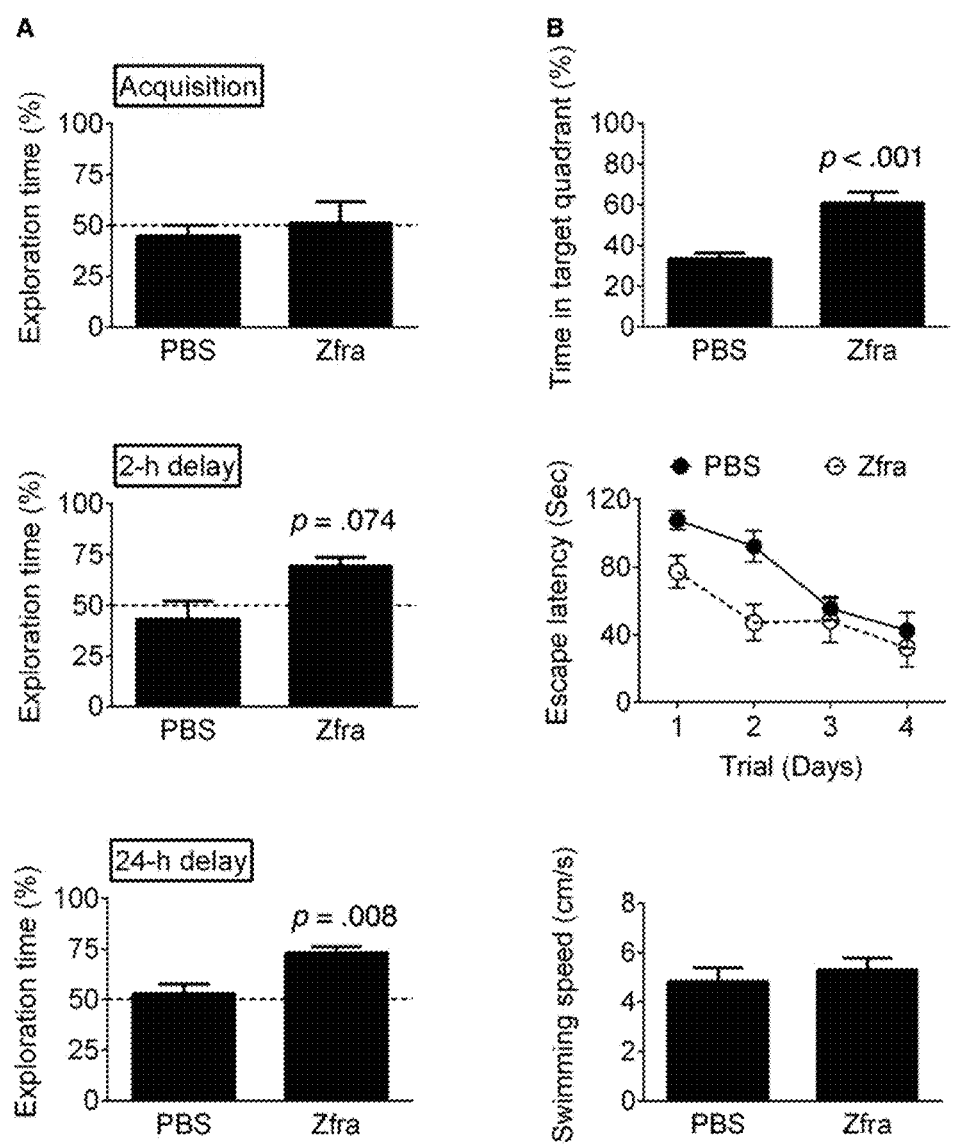
FIG. 1 includes diagrams showing effect of Zfra peptide on learning and memory of 3×Tg mice. (A) The nonspatial learning and memory were determined by novel object recognition task. The abilities of nonspatial memory are expressed as the percentages of novel object exploring time (time spent on novel object/time spent on both objects) during acquisition, short-term (2 hours) delay, and long-term (24 hours) delay (PBS group, n=6; Zfra group, n=5). (B) The spatial learning and memory were determined by Morris Water Maze: latency of training sessions; probe test in water maze; swimming speeds. Statistics: Zfra versus respective PBS group, two-tailed Mann-Whitney test (PBS group, n=12; Zfra group, n=10).

Zfra Rescues the Age-Related Decline of Hippocampus-Dependent Memory in 3×Tg-AD Mice A triple-transgenic mouse (3×Tg) model of AD, expressing mutant Psen1 (M146V), APPSwe, and tau (P301L), was used. Zfra$_{4-10}$ peptide was synthesized (>95% pure) and freshly prepared before use. One week after four injections with Zfra$_{4-10}$ via tail veins, 11-month-old 3×Tg mice were subjected to novel object recognition test for hippocampus-dependent, nonspatial learning and memory. During the 5-minute acquisition phase, both the sham and Zfra mice spent approximately equal exploring times on each object (FIG. 1, Mann-Whitney U=10, P>0.5), indicating no position preferences in the task environment. In the short-term memory task (2 hours after the acquisition phase), the Zfra group showed a marginal, but not significant, increase in the exploring times of the novel object (FIG. 1A, Mann-Whitney U=3, P=0.074), whereas in the long-term memory task (24 hours after the acquisition phase), the novel object exploring times of the Zfra group were significantly higher than those of the sham group (FIG. 1A Mann-Whitney U=2, P=0.008). These results suggest that the hippocampus-dependent, nonspatial long-term memory of 3×Tg mice was increased by Zfra treatment. That is, higher exploring times with the novel object means better memory performance.

One day after the novel object recognition test, the Zfra- and sham-treated 3×Tg mice were subjected to Morris water maze to evaluate the hippocampus-dependent, spatial learning and memory. Both the sham and Zfra groups showed a time-dependent decrease of escape latency (FIG. 1B; F=4.9, df 3/32, P=0.006). Furthermore, the escape latencies were comparable between these two groups (FIG. 1B; F=0.2, df 1/32, P>0.5), indicating that the learning capabilities were not affected by Zfra treatment. In the probe test with the platform removed, the Zfra mice spent more time in the targeted quadrant than that of sham mice (FIG. 1B; Mann-Whitney U=2, P<0.001). The swim velocities in these two groups were similar (FIG. 1B; Mann-Whitney U=11, P>0.5).

Zfra Reduces the AD-Related Pathologies in 3×Tg Mice

Figure 2:
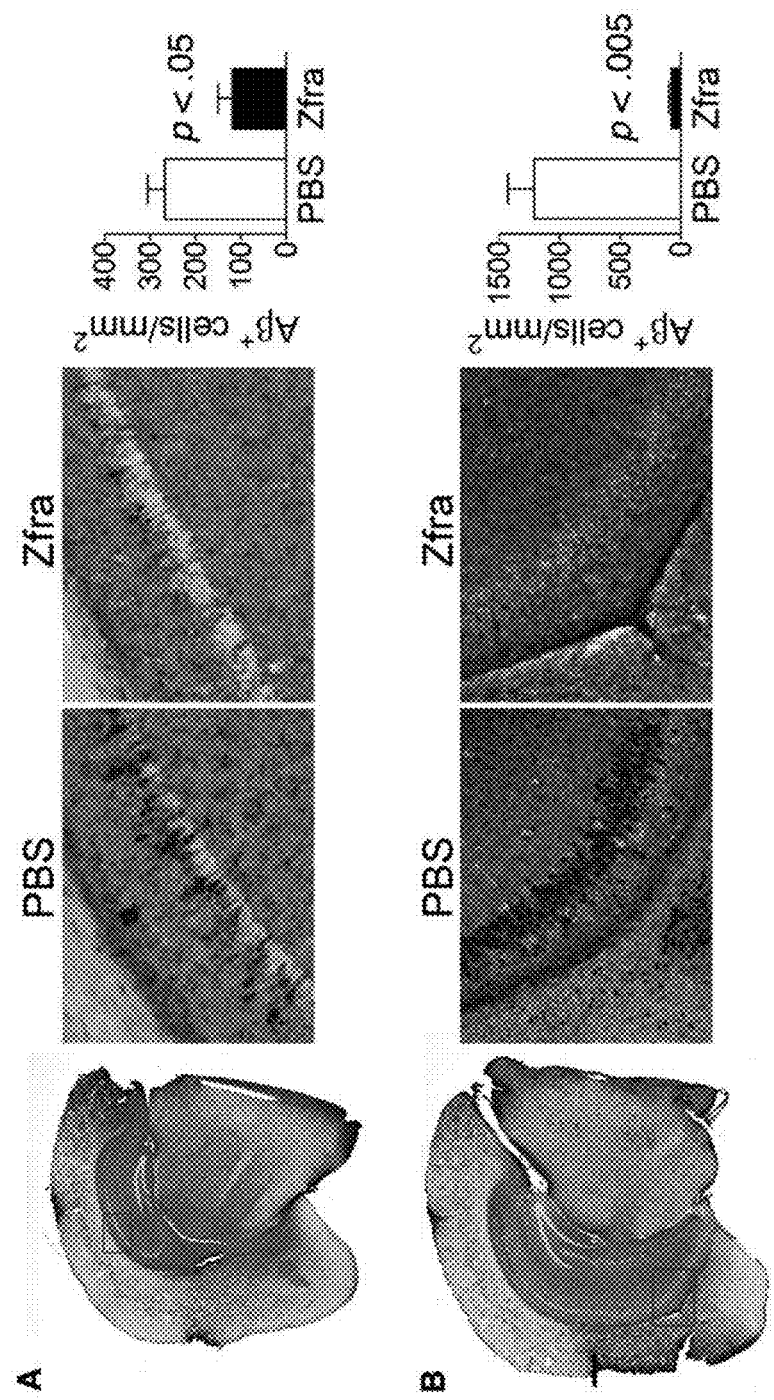
FIG. 2 includes photos and diagrams showing effect of Zfra peptide on Aβ deposition in 3×Tg mice. Representative micrographs of Aβ-positive cells are shown on the left panels, the boxed regions are enlarged and shown on the middle, and the quantitative results are shown on the right. (A) Dorsal hippocampus. (B) Ventral hippocampus. *$P<0.05$ versus respective PBS group, two-tailed unpaired t-test (PBS group, n=3; Zfra group, n=5). Also, representative micrographs of cortical Aβ plaques (white arrows) are shown for the PBS controls and Zfra-treated mice on the left panel (C), and the data quantified on the right. Statistics.
Figure 2:
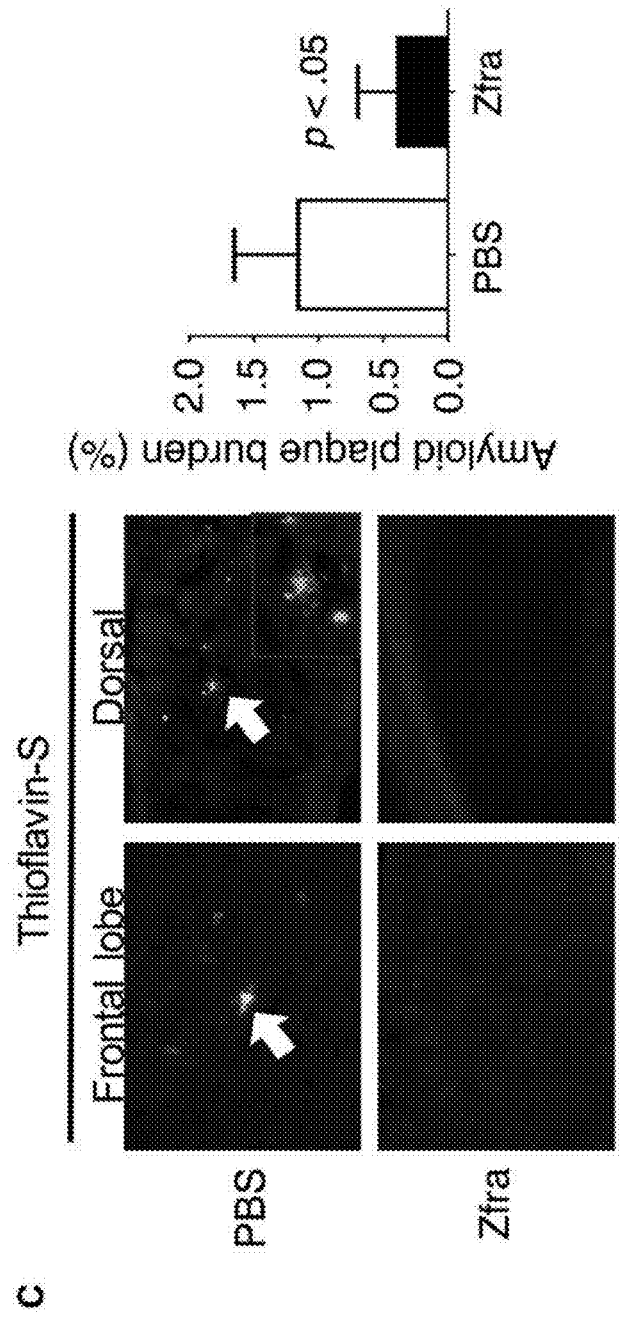

Zfra treatment significantly reduced the numbers of Aβ-positive cells in the dorsal and ventral hippocampi of the 3×Tg mice (FIGS. 2A and B). As stained with thioflavin-S, the presence of cortical Aβ plaques was found in the 10-month-old 3×Tg mice, and Zfra significantly suppressed the plaque formation (FIG. 2C). Furthermore, the relative levels of pS412-tau were also increased in the dorsal and ventral hippocampi of the 3×Tg mice (FIG. 3). Detail analysis of the expression patterns of pS412-tau revealed that the elevated pS412-tau signals mainly localized in the stratum oriens and stratum radiatum of the hippocampus, and Zfra significantly reduced the expression in both regions (FIGS. 3A and B). These results are in agreement with the findings of AD pathology that neurofibrillary tau burden in the hippocampus are frequently restricted to the stratum radiatum and stratum lacunosum. By using specific pT181-tau antibody for PHF-tau, tau aggregates are shown in the cortex and Zfra significantly blocked the aggregation (FIG. 3C). Recently, we demonstrated that TPC6AΔ, an intra-N-terminal deletion of TPC6A, forms cortical plaques starting from mid-ages of normal humans. Zfra significantly suppressed the expression of intracellular pS35-TPC6AΔ and blocked the formation of extracellular pS35-TPC6AΔ plaques (FIG. 3D). SH3GLB2 undergoes self-polymerization via BAR domain. Zfra effectively blocked the aggregation of SH3GLB2 by ~70% (FIG. 3E).

Zfra does not Induce Neurogenesis in 3×Tg Mice

We examined whether Zfra-mediated restoration of memory and behavioral deficits in the 3×Tg mice is involved in neurogenesis. Zfra treatment did not change the number of BrdU$^+$ cells (t=0.4, P>0.5) in the subgranular zone of hippocampus in the 3×Tg mice (control: 18.5±6.5, n=3; Zfra: 22.3±6.7, n=5; two-tailed Student t-test: t=0.4, P>0.5), indicating that no neurogenesis occurs.

Zfra Suppresses Melanoma Growth and Melanoma-Induced Neurodegeneration in the Brain, which Correlates with Suppression of Ser14 Phosphorylation of WWOX Growing tumors, for example, melanoma and glioblastoma, are shown to induce neurodegeneration in vivo. Nude mice received Zfra$_{4-10}$ via tail veins for 3 consecutive weeks and then allowed to rest for a week, followed by inoculating melanoma B16F10 cells on both flanks. Melanoma grew as a solid tumor in the skin and induced apoptosis of pyramidal neurons, possessing condensed cell body and nuclei, in the hippocampi of control mice (97±2% apoptotic nuclei), whereas Zfra-pretreated mice had no neuronal death (0±1% apoptotic nuclei) (FIG. 4A; top panel). The blocking of neuronal death correlates with Zfra-mediated significant suppression of Ser14 phosphorylation of WWOX (pS14-WWOX; 87±5% suppression, n=3), compared to controls (2±3% suppression, n=3). Furthermore, no suppression of Tyr33 phosphorylation in WWOX by Zfra was observed (2±6% suppression, n=3; data not shown). B16F10 cells did not appear to migrate to the brain (FIG. 4A).

In the cortex, B16F10 induced the formation of TPC6AΔ-containing plaques in the control mice, but not in the Zfra-treated mice (FIG. 4A; bottom panel). The tissue section was stained with a specific antibody against TRAPPC6AΔ. TRAPPC6AΔ binds TIAF1, and the complex forms plaques in the extracellular matrix of brain cortex.

In agreement with our previous report, Zfra$_{4-10}$ blocked B16F10 metastasis to the lung (FIG. 4B). Zfra-treated mice exhibited inhibition of Ser14 phosphorylation of WWOX in the lung by greater than 72±6% (n=3). Zfra$_{4-10}$ did not suppress the phosphorylation in Tyr33 in WWOX (5±3%, n=3). Tyr33 phosphorylation is a marker for WWOX activation for nuclear accumulation and inducing apoptosis when overexpressed. In control mice, pSer14-WWOX was expressed in the lung, and B16F10 cells infiltrated in this organ successfully (data not shown). Together, there is a positive correlation between the expression of pS14-WWOX and the occurrence of cancer growth and neurodegeneration in the hippocampus and plaque formation in the cortex. Comparable results were observed using the full-length Zfra$_{1-31}$ in similar experiments (data not shown).

Wwox Heterozygous Mice Exhibit Enhanced Memory Decline

WWOX plays a critical role in the development of neural diseases and degeneration. In light of the aforementioned observations (FIG. 4), we determined that Wwox heterozygous mice exhibited an age-related faster decline in both short- and long-term memories than those in 3×Tg mice, as determined by novel object recognition tests (FIGS. 4C and D).

Zfra Blocks Aggregation of Aβ and Serine-Containing TPC6A Segments In Vitro

We investigated whether Zfra blocks Aβ and TPC6AΔ aggregation in vitro. By mixing Zfra and Aβ together (100 μM each peptide) and incubated in the room temperature for 24 hours or less, we showed that full-length Zfra or red-fluorescent TMR-Zfra blocked the aggregation of Aβ42 in vitro (FIG. A). As a negative control, Aβ40 was used (FIG. 5A).

To determine how TPC6AΔ becomes aggregated in vivo (FIG. 4B), we selected serine-containing TPC6AΔ segments and made peptides, including TPC6AΔ$_{24-38}$, pS35-TPC6AΔ$_{24-38}$, and TPC6AΔ$_{84-100}$. The reason for choosing serine-containing segments is that these regions tend to undergo aggregation. For example, when the aforementioned peptides were suspended in PBS, they became aggregated (FIG. 5B). Little or no aggregations were shown when these peptides were suspended in Milli-Q water (FIG. 5B). By mixing these TPC6AΔ peptides with Zfra$_{4-10}$, Zfra$_{4-10}$ effectively blocked the aggregation of TPC6AΔ peptides (FIG. 5B). These observations suggest that Zfra$_{4-10}$ blocks TPC6AΔ aggregation in vivo via interactions with the serine-containing TPC6AΔ segments.

Under similar conditions, we synthesized serine-containing WWOX$_{7-21}$, WWOX$_{286-299}$, and ANKRD40$_{266-281}$ peptides, along with specific phosphorylation at Ser14, Tyr287, and Ser271, respectively. Without phosphorylation, these peptides polymerized in PBS, and Zfra$_{4-10}$ effectively blocked the polymerization or aggregation (FIG. 5C). ANKRD40 is Ankyrin Repeat Domain 40, whose function is largely unknown. Phosphorylation in WWOX$_{7-21}$ and ANKRD40$_{266-281}$ reduced their extent of polymerization in PBS, and Zfra$_{4-10}$ had apparent effects (FIG. 5C). However, pY287-WWOX$_{286-299}$ became aggregated in PBS and Zfra$_{4-10}$ did not effectively block the aggregation (FIG. 5C).

Zfra Covalently Cross-Links Cellular Proteins and Accelerates their Degradation

To continue to investigate how Zfra reduces protein aggregation in vivo, we examined whether Zfra interacts with cytosolic proteins and accelerates protein degradation. Zfra peptide at high concentrations may undergo self-polymerization especially in PBS. When full-length Zfra$_{1-31}$ peptide (~85% pure; >1 mM) was resuspended in PBS, it underwent self-polymerization with increasing molecular sizes from 3.5 kDa up to 78 and 80 kDa, as analyzed by reducing SDS-PAGE (see the vertical arrow at lane 10, and also lanes 1, 4, and 7; FIG. 6A). Zfra-deficient human breast MCF7 cells were used. Cell lysates were prepared and incubated with Zfra$_{1-31}$, in the presence or absence of a proteasome inhibitor MG-132 and an aliquot of a cocktail of protease inhibitors. The results showed that Zfra-bound cellular proteins as it migrated higher than 3.5 kDa, and the complexes resisted dissociation by SDS and β-mercaptoethanol. We hereby designated the Zfra-bound proteins are "zfrated." The zfrated proteins were degraded with time of incubation (FIG. 6A). Notably, MG-132 did not block but enhanced the protein degradation (see the 30-kDa protein in lanes 2 and 3), suggesting that the ubiquitin/proteasome system is not involved in the degradation process (FIG. 6A). In addition, zfrated proteins from the whole cell lysates or immunoprecipitation did not contain ubiquitin, as determined by antibodies against ubiquitin, and ubiquitin with K48 or K63 acetylation (data not shown).

Similarly, Zfra-negative DU145 cells were exposed to UV light and incubated for 30 minutes at 37° C. Whole cell lysates were prepared in the presence of a cocktail of protease inhibitors. Incubation of the cell lysates with Zfra rapidly increased zfration of cellular proteins (e.g., 78, 80, 200 kDa, and many minor band) in 1-20 minutes, as determined by reducing SDS-PAGE (FIG. 6B). Despite the presence of protease inhibitors, the protein complexes underwent degradation approximately by 60% in 40 minutes and near 95% in 1-2 hours at 37° C. (FIG. 6C). The observations suggest the presence of unidentified proteases in degrading the zfrated proteins. Exogenous Zfra alone also underwent degradation. In controls, Zfra-free lysates had significantly retarded degradation in the presence of protease inhibitors (<10% in 1-2 hours).

Murine L929 fibroblasts express low levels of Zfra. UV irradiation or TNF-α upregulates the expression of Zfra. Aliquots of the lysates of L929 cells were incubated with. Zfra$_{1-31}$ peptide for 30 minutes at 37° C. (in PBS). Two proteins of 80 and 22 kDa were rapidly zfrated and then degraded in 30 minutes (FIG. 6D). In addition, a 30-kDa protein became zfrated during incubation for 30 minutes (FIG. 6D). We further verified zfration using purified small recombinant proteins. Zfra caused zfration of recombinant His-Tau in PBS, as determined by reducing SDS-PAGE (FIG. 6E).

Endogenous Zfra Hinds Tau and Aβ in the AD Hippocampus

We examined the levels of Zfra in the hippocampal extracts from postmortem AD patients and normal controls. By immunofluorescence and confocal microscopy, Zfra was shown to colocalize with Aβ and PHF (paired helical filaments)-tau (FIG. A-D). Binding of Zfra with Aβ and PIM-tau was verified by Förster resonance energy transfer (FRET) analysis. In most cases, Zfra bound strongly with Aβ and PHF-tau, or no binding at all (see FRETc) (FIG. 7E). Confocal microscopy analysis revealed the colocalization of Zfra with Aβ (FIG. 7C). Similarly, by using postmortem human soluble hippocampal extracts, endogenous Zfra was shown to complex, in part, with Aβ, as determined by nonreducing SDS-PAGE (data not shown). By filter retardation assay using insoluble hippocampal extracts, aggregation of Zfra and pSer8-Zfra occurred greatly by 45% and 85% increases, respectively, in the older AD patients (81±9.7 years old; n=70), as compared to younger nondemented controls (60±13.3 years old; n=46) (FIG. 7F). In the AD hippocampi, Aβ levels were raised by 170%.

Zfra Blocks TNF-Mediated Activation of NF-κB Promoter

NF-κB plays a crucial role in the pathogenesis of AD. We examined whether Zfra blocks NF-κB promoter activation using a fluorescent reporter assay. COST fibroblasts were transfected with a GFP-tagged NF-κB promoter reporter construct and/or an ECFP-Zfra construct. In controls, cells were transfected with a negative or a positive GFP control vector, or an empty ECFP vector. These cells were exposed to TNF-α for 24 hours. Zfra blocked TNF-α-mediated activation of NF-κB promoter in cells expressing ECFP-Zfra and the promoter construct (FIG. 7G). In controls, TNF-α-activated NE-KB promoter in cells transfected the promoter construct, in the presence or absence of ECFP (FIG. 7G).

Zfra Induces Z Cells to Relocate Out of the Spleen and does not Appear to Migrate to the Brain When immune-competent or deficient mice receive Zfra via tail vein injections, circulating Zfra is mainly deposited in the spleen and fluoresced strongly due to aggregation. Zfra activates Z cell to induce memory response against the growth of many types of cancer cells. Residential Z cells are localized in the peripheral areas of germinal centers in the 3×Tg mice, and that Zfra drove the cells out of the spleen (FIG. 8A). Similar results were observed in other immune-competent mice (e.g., BALB/c and B6 mice). Z cells did not appear to migrate to the brain, as the signals were barely detectable (FIG. 8B). In the T cell-deficient nude mice, the residential Z cell population exhibited as clusters (FIG. 8C). These mice do not have germinal centers. In response to Zfra, Z cells moved out of the spleen in the nude mice and relocated, in part, in the cancer lesion sites (FIG. 8D). Z cells localized in the lymphatic ducts penetrating in the skin B16F10 tumors (FIG. 8D). In control mice, less Z cells relocated to the tumor lesions.

In summary; we demonstrated here for the first time that Zfra effectively restores the memory capabilities of aging Alzheimer's disease 3×Tg mice. The underlying mechanism is associated, in part, with Zfra inhibition of the aggregation of TPC6AΔ, SH3GLB2, tau, and Aβ in the mouse brains. In vitro assays showed Zfra suppression of TNF-mediated NF-κB activation, suggesting an additional mechanism of Zfra inhibition of inflammatory NF-κB activation in AD brains in vivo.

In the melanoma mouse model, we showed that Zfra blocks neuronal death in the hippocampus and plaque formation in the cortex. No neurogenesis occurs in hippocampal subgranular and subventricular zones. Additional evidence showed that Zfra inhibits the aggregation of Aβ42, TPC6AΔ, and many serine-containing peptides under cell-free conditions. Preliminary data by mass analysis showed that covalent cross-linking between serine residues occurs, especially in the presence of phosphates in the solution (data not shown). Zfra binds cytosolic proteins to accelerate their degradation in vitro, which may reduce the levels of aggregated TPC6AΔ, tau, and Aβ in vivo.

Participation of Z cells in reducing protein aggregation is very likely. Circulating Zfra is mainly deposited in the spleen. We do not exclude the possibility that a small amount of Zfra goes through the blood-brain barrier and targets tau or Aβ for accelerating degradation. A portion of WWOX is present on the cell membrane via interacting with Hyal-2 and Ezrin. Zfra activates Z cells in the spleen probably via the Hyal-2/WWOX/Smad4 pathway. Approximately in 3 weeks or less, these activated Z cells leave the spleen and enter the lymphatic ducts. Conceivably, Z cells secreted cytokines or proteases capable of degrading protein aggregates in the brain. In addition, we have been carrying out transfer of activated Z cells to aging 3xTg mice to validate their function in blocking neurodegeneration.

To gain a better insight regarding how Zfra works in AD brains, we examined hippocampal extractions from postmortem normal individuals and AD patients. We found that upregulation of Zfra, pS8-Zfra, and Aβ in the AD hippocampi occurs and these proteins are found in the insoluble fractions.

In addition, by using Wwox heterozygous mice, we determined that decline of memory is faster than those of 3xTg mice. The observations provide another line of evidence that WWOX is essential in supporting neuronal functions. Knockout Wwox mice have brain developmental defects, ataxia and seizure. They can only survive for less than 30 days. They are not suitable for the intended experiments for memory decline.

As short as seven amino acids, $Zfra_{4-10}$ undergoes self-polymerization and is highly potent in blocking many types of cancer metastasis and growth. $Zfra_{4-10}$ is effective in restoring the memory deficits in 3xTg mice and blocks cancer-associated neurodegeneration. The conserved phosphorylation site Ser8 plays a crucial role in conferring polymerization of $Zfra_{4-10}$. When Zfra peptide is mixed with a serine-containing peptide, polymerization of both peptides is nullified.

Although the present disclosure has been explained in relation to its embodiment, it is to be understood that many other possible modifications and variations can be made without departing from the spirit and scope of the disclosure as hereinafter claimed.

What is claimed is:

1. A method for treating Alzheimer's disease, comprising: administering an effective amount of a zinc finger-like peptide to a subject in need thereof, wherein the zinc finger-like peptide comprises an amino acid sequence of RRSSSCK (SEQ ID NO: 1).

2. The method of claim 1, wherein the amino acid sequence of the zinc finger-like peptide is RRSSSCK (SEQ ID NO: 1).

3. The method of claim 1, wherein the amino acid sequence of the zinc finger-like peptide is MSSRRSSSCK-YCEQDFRAHTQKNAATPFL AN (SEQ ID NO: 2).

* * * * *

```
                         SEQUENCE LISTING

<160> NUMBER OF SEQ ID NOS: 17

<210> SEQ ID NO 1
<211> LENGTH: 7
<212> TYPE: PRT
<213> ORGANISM: Artificial
<220> FEATURE:
<223> OTHER INFORMATION: Synthesized peptide

<400> SEQUENCE: 1

Arg Arg Ser Ser Ser Cys Lys
1               5

<210> SEQ ID NO 2
<211> LENGTH: 31
<212> TYPE: PRT
<213> ORGANISM: Artificial
<220> FEATURE:
<223> OTHER INFORMATION: Synthesized pepetide

<400> SEQUENCE: 2

Met Ser Ser Arg Arg Ser Ser Ser Cys Lys Tyr Cys Glu Gln Asp Phe
1               5                   10                  15

Arg Ala His Thr Gln Lys Asn Ala Ala Thr Pro Phe Leu Ala Asn
            20                  25                  30

<210> SEQ ID NO 3
<211> LENGTH: 15
<212> TYPE: PRT
<213> ORGANISM: Artificial
<220> FEATURE:
<223> OTHER INFORMATION: Synthesized peptide

<400> SEQUENCE: 3

Ala Gly Leu Asp Asp Thr Asp Ser Glu Asp Glu Leu Pro Pro Gly
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthesized peptide
```

```
<220> FEATURE:
<221> NAME/KEY: MOD_RES
<222> LOCATION: (8)..(8)
<223> OTHER INFORMATION: PHOSPHORYLATION

<400> SEQUENCE: 4

Ala Gly Leu Asp Asp Thr Asp Ser Glu Asp Glu Leu Pro Pro Gly
1               5                   10                  15

<210> SEQ ID NO 5
<211> LENGTH: 14
<212> TYPE: PRT
<213> ORGANISM: Artificial
<220> FEATURE:
<223> OTHER INFORMATION: Synthesized peptide

<400> SEQUENCE: 5

Asp Tyr Trp Ala Met Leu Ala Tyr Asn Arg Ser Lys Leu Cys
1               5                   10

<210> SEQ ID NO 6
<211> LENGTH: 14
<212> TYPE: PRT
<213> ORGANISM: Artificial
<220> FEATURE:
<223> OTHER INFORMATION: Synthesized peptide
<220> FEATURE:
<221> NAME/KEY: MOD_RES
<222> LOCATION: (2)..(2)
<223> OTHER INFORMATION: PHOSPHORYLATION

<400> SEQUENCE: 6

Asp Tyr Trp Ala Met Leu Ala Tyr Asn Arg Ser Lys Leu Cys
1               5                   10

<210> SEQ ID NO 7
<211> LENGTH: 15
<212> TYPE: PRT
<213> ORGANISM: Artificial
<220> FEATURE:
<223> OTHER INFORMATION: Synthesized peptide

<400> SEQUENCE: 7

Asp Pro Gly Pro Gly Gly Gln Lys Met Ser Leu Ser Val Leu Glu
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthesized peptide
<220> FEATURE:
<221> NAME/KEY: MOD_RES
<222> LOCATION: (12)..(12)
<223> OTHER INFORMATION: PHOSPHORYLATION

<400> SEQUENCE: 8

Asp Pro Gly Pro Gly Gly Gln Lys Met Ser Leu Ser Val Leu Glu
1               5                   10                  15

<210> SEQ ID NO 9
<211> LENGTH: 16
<212> TYPE: PRT
<213> ORGANISM: Artificial
<220> FEATURE:
<223> OTHER INFORMATION: Synthesized peptide

<400> SEQUENCE: 9
```

```
Lys Asp Leu Trp Val Ala Val Phe Gln Lys Gln Met Asp Ser Leu Arg
1               5                   10                  15
```

<210> SEQ ID NO 10
<211> LENGTH: 16
<212> TYPE: PRT
<213> ORGANISM: Artificial
<220> FEATURE:
<223> OTHER INFORMATION: Synthesized peptide

<400> SEQUENCE: 10

```
Arg Ile Gln Asn Pro Ser Leu Arg Glu Asn Asp Phe Ile Glu Ile Glu
1               5                   10                  15
```

<210> SEQ ID NO 11
<211> LENGTH: 16
<212> TYPE: PRT
<213> ORGANISM: Artificial
<220> FEATURE:
<223> OTHER INFORMATION: Synthesized peptide
<220> FEATURE:
<221> NAME/KEY: MOD_RES
<222> LOCATION: (6)..(6)
<223> OTHER INFORMATION: PHOSPHORYLATION

<400> SEQUENCE: 11

```
Arg Ile Gln Asn Pro Ser Leu Arg Glu Asn Asp Phe Ile Glu Ile Glu
1               5                   10                  15
```

<210> SEQ ID NO 12
<211> LENGTH: 42
<212> TYPE: PRT
<213> ORGANISM: Artificial
<220> FEATURE:
<223> OTHER INFORMATION: Synthesized peptide

<400> SEQUENCE: 12

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40
```

<210> SEQ ID NO 13
<211> LENGTH: 40
<212> TYPE: PRT
<213> ORGANISM: Artificial
<220> FEATURE:
<223> OTHER INFORMATION: Synthesized peptide

<400> SEQUENCE: 13

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val
            35                  40
```

<210> SEQ ID NO 14
<211> LENGTH: 16
<212> TYPE: PRT
<213> ORGANISM: Artificial
<220> FEATURE:
<223> OTHER INFORMATION: Synthesized peptide

```
<400> SEQUENCE: 14

Cys Ala Gly Leu Asp Asp Thr Asp Ser Glu Asp Glu Leu Pro Pro Gly
1               5                   10                  15

<210> SEQ ID NO 15
<211> LENGTH: 16
<212> TYPE: PRT
<213> ORGANISM: Artificial
<220> FEATURE:
<223> OTHER INFORMATION: Synthesized peptide
<220> FEATURE:
<221> NAME/KEY: MOD_RES
<222> LOCATION: (9)..(9)
<223> OTHER INFORMATION: PHOSPHORYLATION

<400> SEQUENCE: 15

Cys Ala Gly Leu Asp Asp Thr Asp Ser Glu Asp Glu Leu Pro Pro Gly
1               5                   10                  15

<210> SEQ ID NO 16
<211> LENGTH: 17
<212> TYPE: PRT
<213> ORGANISM: Artificial
<220> FEATURE:
<223> OTHER INFORMATION: Synthesized peptide

<400> SEQUENCE: 16

Cys Lys Asp Leu Trp Val Ala Val Phe Gln Lys Gln Met Asp Ser Leu
1               5                   10                  15
Arg

<210> SEQ ID NO 17
<211> LENGTH: 17
<212> TYPE: PRT
<213> ORGANISM: Artificial
<220> FEATURE:
<223> OTHER INFORMATION: Synthesized peptide

<400> SEQUENCE: 17

Cys Asp Ala Cys Lys Ala Arg Leu Lys Lys Ala Lys Ala Ala Glu Ala
1               5                   10                  15
Lys
```